US007611907B2

(12) United States Patent
Dickson et al.

(10) Patent No.: US 7,611,907 B2
(45) Date of Patent: Nov. 3, 2009

(54) NANO-SIZED OPTICAL FLUORESCENCE LABELS AND USES THEREOF

(75) Inventors: Robert Martin Dickson, Atlanta, GA (US); Jie Zheng, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 740 days.

(21) Appl. No.: 10/519,267

(22) PCT Filed: Jun. 27, 2003

(86) PCT No.: PCT/US03/20567

§ 371 (c)(1),
(2), (4) Date: Dec. 27, 2004

(87) PCT Pub. No.: WO2004/003558

PCT Pub. Date: Jan. 8, 2004

(65) Prior Publication Data

US 2006/0051878 A1    Mar. 9, 2006

(51) Int. Cl.
*G01N 33/553* (2006.01)
(52) U.S. Cl. .................... 436/525; 436/172; 436/805
(58) Field of Classification Search ........................ None
See application file for complete search history.

(56) References Cited

U.S. PATENT DOCUMENTS

| | | | |
|---|---|---|---|
| 4,313,734 | A | 2/1982 | Leuvering |
| 4,744,760 | A | 5/1988 | Molday |
| 5,759,518 | A | 6/1998 | Schmitt-Willich et al. |
| 6,224,898 | B1 | 5/2001 | Balogh et al. |
| 6,475,994 | B2 | 11/2002 | Tomalia et al. |
| 6,599,631 | B2 | 7/2003 | Kambe et al. |
| 6,664,315 | B2 | 12/2003 | Tomalia et al. |
| 2001/0011109 | A1 | 8/2001 | Tomalia et al. |
| 2004/0070094 | A1 | 4/2004 | Tomalia et al. |
| 2004/0072937 | A1 | 4/2004 | Tomalia et al. |
| 2004/0151689 | A1 | 8/2004 | Tomalia et al. |

FOREIGN PATENT DOCUMENTS

WO    WO 98/30604    7/1998

OTHER PUBLICATIONS

Yu Weiyong, et al., "Preparation and Characterization of Ruthenium Metal Nanocluster Stabilized with Polymer," J. Chin. Electr. Microsc. Soc., vol. 17, No. 5, pp. 629-630, 1998.
Balogh, et al., (1998) "Poly(amidoamine) Dendrimer-Templated Nanocomposites. 1. Synthesis of Zerovalent Copper Nanoclusters", *J. Am. Chem. Soc.*, 120:7355-7356.
Bouchama, et al., (2004) "Self-Assembly of a Hexagonal Phase of Wormlike Micelles Containing Metal Nanoclusters". *Langmuir*, 20:477-483.
Brousseau III., et al., (1999) "Assembly of Phenylacetylene-Bridged Gold Nanocluster Dimers and Trimers", *Adv. Mater.*, 11:447-449.
Chechik, et al., (1999) "Self-Assembled Inverted Micelles Prepared from a Dendrimer Template: Phase Transfer of Encapsulated Guests", *J. Am. Chem. Soc.*,121:4910-4911.
Floriano, et al., (2001) "Cu(0) Nanoclusters Derived from Poly(propylene imine) Dendrimer Complexes of Cu(II)", *J. Am. Chem. Soc.*, 123:10545-10553.
Garcia, et al., (1999) "Preparation and Characterization of Dendrimer-Gold Colloid Nanocomposites", *Anal. Chem.*, 71::256-258.
Gröhn, et al., (1998) "Nanoparticle Formation within Dendrimer-Containing Polymer Networks: Route to New Organic-Inorganic Hybrid Materials", *Macromolecules*, 34:2179-2185.
Pádua, et al., (1997) "On the Geometry and Conformation of Starburst Dendrimers", *Journal of Mathematical Chemistry*, 22: 97-106.
Petty, et al., (2004) "DNA-Templated Ag Nanocluster Formation", *J. Am. Chem. Soc.*, 126:5207-5212.
Slocik, et al., (2002) "Monoclonal Antibody Recognition of Histidine-Rich Peptide Encapsulated Nanoclusters", *Nano Letters, American Chemical Society*, 2:169-173.
Slocik, et al., (2003) "Biomimetic Mineralization of Noble Metal Nanoclusters", *Biomacromolecules*, 4:1135-1141.
Storhoff, et al., (1999) "Programmed Materials Synthesis with DNA", *Chem. Rev.*, 99:1849-1862.
Velarde-Ortiz, et al., (2002) "A Poly(propylene imine) (DAB-Am-64) Dendrimer as $Cu^{2+}$ Chelator for the Synthesis of Copper Oxide Clusters Embedded in Sol-Gel Derived Matrixes", *Chem. Mater.*, 14:858-866.
Zhao, et al., (1998) "Preparation of Cu Nanoclusters within Dendrimer Templates", *J. Am. Chem. Soc.*,120:877-4878.
Zhao, et al., (1999) "Dendrimer-Encapsulated Pt Nanoparticles: Synthesis, Characterization, and Applications to Catalysis", *Advanced Materials*,11:217-220.
Zhao, et al., (1999) "Intradendrimer Exchange of Metal Nanoparticles," *Chem. Mater.*, 11:3379-3385.
Clark et al., 2000, "Second Harmonic Generation Properties of Fluorescent Polymer-Encapsulated Gold Nanoparticles," J. Am. Chem. Soc., 111:10234-10235.
Garcia et al., 1999, "Preparation and Characterization of Dendrimer—Gold Colloid Nanocomposites," Anal. Chem., 71:256-258.
Grohn et al., 2001, "Nanoparticle Formation within Dendrimer-Containing Polymer Networks: Route to new Organic-Inorganic Hybrid Materials," Macromolecules, 34:2179-2185.
Huang et al., 2001, "Visible Luminescence of Water-Soluble Monolayer-Protected Gold Clusters," J. Phys. Chem. B, 105:12498-12502.

(Continued)

*Primary Examiner*—Christopher L Chin
(74) *Attorney, Agent, or Firm*—Sutherland Asbill & Brennan LLP

(57) ABSTRACT

A composition is disclosed which is capable of being used for detection, comprising an encapsulated noble metal nanocluster. Methods for preparing the encapsulated noble metal nanoclusters, and methods of using the encapsulated noble metal nanoclusters are also disclosed. The noble metal nanoclusters are preferably encapsulated by a dendrimer or a peptide. The encapsulated noble metal nanoclusters have a characteristic spectral emission, wherein said spectral emission is varied by controlling the nature of the encapsulating material, such as by controlling the size of the nanocluster and/or the generation of the dendrimer, and wherein said emission is used to provide information about a biological state.

30 Claims, 5 Drawing Sheets

OTHER PUBLICATIONS

Pagliari et al., 2000, "Enantioselective Sensing of Amino Acids by Copper(II) Complexes of Phenylalanine-Based Fluorescent beta-cyclodescrins," Tetrahedron Letters, 41:3691-3695.

Zhao et al., "Intradendrimer Exchange of Metal Nanoparticles," Chem. Mater., 11:3379-3385, 1999.

European Supplementary Search Report for EP 03 74 23334 dated Sep. 9, 2008.

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala His His Ala His His Ala Ala Asp
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: 6X-His tag

<400> SEQUENCE: 2

His His His His His His
1               5
```

NANO-SIZED OPTICAL FLUORESCENCE LABELS AND USES THEREOF

BACKGROUND OF THE INVENTION

1. Field of the Invention

The present invention relates to the creation of new classes of fluorescent/luminescent probes based on metal cluster fluorescence, methods of preparing such probes, and methods of use thereof.

2. Background Art

Single molecule fluorescence microscopy studies present an extreme limit in which weak signals must be observed on essentially zero background. Such optical methods relying on high-intensity laser excitation of highly emissive and robust fluorophores require extremely efficient background rejection. Relying on the introduction of artificial labels to identify the particular protein or structure of interest, fluorescence based methods suffer from two additional problems—photobleaching (loss of signal due to probe destruction) and autofluorescence (naturally occurring background fluorescence from native species within biological media). Even with these problems, fluorescence microscopy remains the primary optical method with potential for single molecule and chemical sensitivity while imaging biological media.

Most in vitro fluorescent labeling is performed through standard chemical coupling of either N-succinimidyl ester-conjugated dyes to free, solvent-exposed amines (often on lysine residues) or maleimide-conjugated dyes to thiols on either naturally occurring or genetically introduced solvent-exposed cysteines. These two coupling chemistries continue to be extremely useful in attaching small, highly fluorescent dyes to proteins of interest. Such fluorescent biomaterials are then adequate for in vitro single molecule studies, or they can be re-introduced into cells in high concentration either through microinjection or other membrane transport methods to perform bulk fluorescence studies of the protein of interest within whole cells. Not only can protein function be altered both by the size and point of attachment of the fluorescent label, but also often because of the coupling chemistry used, the site of the fluorescent labeling is not accurately known. Thus, the smallest possible genetically programmed label would be highly advantageous.

Additionally, in biological systems, the autofluorescent background from flavins, porphyrins, and all other weakly fluorescent naturally occurring species can produce a large background that interferes with laser-induced fluorescence signals. Because of these problems, studying dynamics of few copies of proteins within living systems requires the development of new fluorescent probes that absorb and emit so strongly and without significant photobleaching such that they can be easily observed with extremely weak incoherent illumination for long times. Such illumination would enable preferential excitation of the fluorophores of interest relative to that of weak background signals. Additionally, the weaker illumination would preserve biological viability by minimizing phototoxicity effects. Unfortunately, single molecule sensitivities are as of yet difficult to attain in such high background in vivo studies and are often difficult to observe even in lower background in vitro studies.

Because of signal to noise constraints, single molecule studies are limited to fluorescence-based assays with all its associated difficulties. While single molecule methods have been effective in "peeling back" the ensemble average to examine environmental and mechanistic heterogeneity, current techniques require expensive laser-based equipment, specialized synthetic methods, and are still fundamentally limited by the poor optical properties or bioincompatibility of available fluorescent labels.

Several key experiments have uniquely demonstrated the ability of single molecule microscopies to unravel the crucial steps leading to biological activity (Lu et al., Science 1998, 282:1877-1882; Dickson et al., Nature 1997, 388:355-358; Funatsu et al., Nature 1995, 374:555-59; Ha et al., Proc. Nat. Acad. Sci., USA 1996, 93, 6264-6268; Vale et al., Nature 1996, 380:451-453; Deniz et al., Proc. Natl. Acad. Sci., USA 2000, 97:5179-5184; Ha et al., Proc. Natl. Acad. Sci. USA 1999, 96:893-898; Harada et al., Biophys. J. 1999, 76:709-715; Kinosita, Biophys. J. 2000, 78:149Wkshp). Most dramatic in studies of individual motor protein motion, mechanistic insights into protein function and substeps within biomechanical cycles can be directly visualized, without the need of difficult external synchronization (Funatsu et al., Nature 1995, 374:555-59; Vale et al., Nature 1996, 380:451-453; Kinosita, Biophys. J. 2000, 78:149Wkshp; Yanagida et al., Curr. Opin. Cell Biol. 2000, 12:20-25). Even biomolecule folding has been probed to unravel pathways leading to both misfolded and folded states (Deniz et al., Proc. Natl. Acad. Sci., USA 2000, 97:5179-5184; Ha et al., Proc. Natl. Acad. Sci. USA 1999, 96:893-898). Now that orientational (Bartko & Dickson, J. Phys. Chem. B 1999, 103:3053-3056; Bartko & Dickson, J. Phys. Chem. B 1999, 103:11237-11241; Bartko et al., Chem. Phys. Lett. 2002, 358:459-465; Hollars & Dunn, J. Chem. Phys. 2000, 112:7822-7830) and fluorescence resonance energy transfer (FRET) methods (Weiss, Science 1999, 283:1676-1683) have been developed on the single molecule level, many more experiments are now possible. Unfortunately in all single molecule studies, researchers are relegated to artificial fluorescent labeling of proteins of interest and limited to in vitro observation. Re-introduction of labeled proteins into the cell has yet to produce viable in vivo single molecule signals due to the large autofluorescent background and poor photostability of organic fluorophores.

Single molecules also have many inherently undesirable properties that limit the timescales of experiments. Excitation rates must be very high to yield biologically relevant information with reasonable time resolution (ms to seconds) and good signal to noise. Because the absorption cross-section (i.e. extinction coefficient, $\epsilon$) of the best organic fluorophores is only $\sim 10^{-16}$ cm$^2$ (i.e. $\epsilon \sim 10^5$ M$^{-1}$ cm$^{-1}$) at room temperature (Macklin et al., Science 1996, 272:255-258), high intensity laser excitation must be utilized for single molecule fluorescence studies. Additionally, organic molecules can only withstand $\sim 10^7$ excitation cycles before they photochemically decompose (Dickson et al., Nature 1997, 388:355-358; Lu & Xie, Nature 1997, 385:143-146; Macklin et al., Science 1996, 272:255-258). At $10^6$ excitations/second (using $\sim 5$ kW/cm$^2$ excitation intensity and a typical collection/detection efficiency of 5%), this limits the time resolution to $\sim 1$ ms (with an idealized signal to noise ratio of $\sim 7$), and the average total time to follow an individual molecule before photobleaching of $\sim 10$ seconds. While this can be a very large amount of data on very biologically relevant timescales, many of the excitation cycles end up being consumed by finding the molecules of interest before collecting data. Clearly, while reduction of oxygen can often increase the time before photobleaching, the photostability and overall brightness of the organic dyes limit all biological single molecule experiments. Thus, advances in fluorophore properties will be crucial to the continued success of all single molecule optical studies in biological systems.

Requiring similar coupling chemistry to that of organic fluorophores, water soluble II-VI quantum dots have recently been proposed and demonstrated as biological labels (Bruchez et al., Science 1998, 281:2013-2016; Chan & Nie, Science 1998, 281:2016-2018; Zhang et al., Analyst 2000, 125:1029-1031). Materials such as CdSe with protective and stabilizing ZnS overcoatings have size dependent optical properties and can be synthesized with very narrow size distributions (Murray et al., Z. Phys. D-Atoms Mol. Clusters 1993, 26:S231-S233; Murray et al., J. Am. Chem. Soc. 1993, 115:8706-8715; Peng et al., Nature 2000, 404:59-61). The strong absorption, spectral stability, and size-tunable narrow emission of these nanomaterials suggest exciting possibilities in biolabeling once further chemistry on the outer ZnS layer is performed to make these materials water-soluble (Rodriguez-Viejo et al., J. Appl. Phys. 2000, 87:8526-8534; Dabbousi et al., J. Phys. Chem. B 1997, 101:9463-9475). Because surface passivation is incredibly important in overall quantum dot optical properties, much care must be spent on quantum dot surface passivation and derivitization such that they can be reproducibly conjugated to proteins with predictable optical responses (Bruchez et al., Science 1998, 281:2013-2016; Chan & Nie, Science 1998, 281:2016-2018; Rodriguez-Viejo et al., J. Appl. Phys. 2000, 87:8526-8534; Dabbousi et al., J. Phys. Chem. B 1997, 101:9463-9475; Nirmal & Brus, Acc. Chem. Res. 1999, 32:407-414; Nirmal et al., Nature 1996, 383:802-804). In fact, successful implementation of water solubilization and surface passivation are only now beginning to bear fruit (Dubertret et al., Science 2002, 298:1759-1762; Jaiswal et al., Nat. Biotechnol. 2003, 21:47-51; Wu et al., Nat. Biotechnol. 2003, 21:41-46; Sutherland, Curr. Opin. Solid State Mat. Sci. 2002, 6:365-370; Gao et al., J. Biomed. Opt. 2002, 7:532-537; Mattoussi et al., J. Am. Chem. Soc. 2000, 122:12142-12150).

While quite promising due to their bright and very narrow size-dependent emission, multiple problems with using CdSe as biological labels still exist. Their synthesis requires high temperature methods using highly toxic precursors, they are comparable to the size of proteins that they may label (2-6 nm in diameter), and they suffer from the same need to externally label proteins of interest and possibly re-introduce the labeled proteins into cells. Thus, while the strong oscillator strengths enable quantum dots to be easily observed with weak mercury lamp excitation, thereby avoiding much of the more weakly absorbing autofluorescent background, they are still not an ideal solution to in vivo or in vitro single molecule studies.

Ideally, one would want the smallest possible genetically programmed label to be expressed on or adjacent to the protein of interest. Such an ideal label would need to have sufficiently strong absorption and emission as well as outstanding photostability to enable long time single molecule observation with high time resolution, even in the presence of high background fluorescence. Such a fluorescent probe does not yet exist. Currently the best available options due to being composed solely of amino acids, green fluorescent protein (GFP; Dickson et al., Nature 1997, 388:355-358; Heim, Proc. Nat. Acad. Sci, USA 1994, 91:12501-04; Ormo et al., Science 1996, 273:1392-5; Chattoraj et al., Proc. Nat. Acad. Sci, USA 1996, 93:362-67; Brejc et al., Proc. Nat. Acad. Sci, USA 1997, 94:2306-11; Cubitt et al., Trends in Biochem. Sci. 1995, 20:448-55; Kain & Kitts, Methods Mol. Biol. 1997, 63:305-24) and DsRed (Gross et al., Proc. Natl. Acad. Sci., USA 2000, 97:11990-11995; Jakobs et al., FEBS Lett. 2000, 479:131-135; Wall et al; Nat. Struct. Biol. 2000, 7:1133-1138; Yarbrough et al., Proc. Natl. Acad. Sci., USA 2001, 98:462-467) are excellent in vivo labels, and have been observed on the single molecule level in in vitro studies by many authors (Dickson et al., Nature 1997, 388:355-358; Malvezzi-Campeggi et al., Biophys. J. 2001, 81:1776-1785; Garcia-Parajo et al., Proc. Natl. Acad. Sci., USA 2000, 97:7237-7242; Cotlet et al., Chem. Phys. Lett. 2001, 336, 415-423; Lounis et al., J. Phys. Chem. B 2001, 105:5048-5054; Garcia-Parajo et al., Pure Appl. Chem. 2001, 73:431-434; Garcia-Parajo et al., ChemPhysChem 2001, 2:347-360; Garcia-Parajo et al., Proc. Natl. Acad. Sci., USA 2001, 98:14392-14397; Blum et al., Chem. Phys. Lett. 2002, 362: 355-361).

In one of the first such studies, GFP's blinking and optical switching abilities have been studied as photons were used to shuttle the GFP chromophore between two different optically accessible states (Dickson et al., Nature 1997, 388:355-358). Unfortunately, while GFP can be specifically attached to the N or C terminus of any protein and expressed in vivo as a highly fluorescent label, problems, especially on the single molecule level, still remain. GFP is 27 kD or ~4 nm in diameter (Ormo et al., Science 1996, 273:1392-5; Cubitt et al., Trends in Biochem. Sci. 1995, 20:448-55), and can therefore be a large perturbation to the protein to which it is attached. In addition, emission only occurs once GFP has folded into its final conformation, a process that can take up to ~1 hour and, while examples of GFP labeling have been reported within all regions of different cells, sometimes GFP does not properly fold under a given set of conditions (Heim, Proc. Nat. Acad. Sci, USA 1994, 91:12501-04; Cubitt et al., Trends in Biochem. Sci. 1995, 20:448-55). Additionally, when considering single molecule studies, its emission significantly overlaps with the autofluorescent background, but its emission intensity is only comparable to standard exogenous organic dyes, thereby making in vivo single molecule studies very challenging. While largely insensitive to oxygen, it also typically bleaches after ~$10^7$ excitation cycles, similar to standard organic dyes (Dickson et al., Nature 1997, 388:355-358). DsRed partially circumvents the issue of overlap with autofluorescent background, but while the red-shifted emission of DsRed relative to that of GFP could be an advantage, its comparable fluorescence intensity and tendency to form quadruplexes even at extremely low concentrations may further limit its use as an ideal biological label (Lounis et al., J. Phys. Chem. B 2001, 105:5048-5054; Garcia-Parajo et al., ChemPhysChem 2001, 2:347-360; Verkhusha et al., J. Biol. Chem. 2001, 276:29621-29624; Sacchetti et al., FEBS Lett. 2002, 525:13-19). Thus, the ideal label would combine the strong absorption, emission, and photostability of inorganic quantum dots, the small size and simple attachment chemistry of organic dyes, or preferably, like GFP and DsRed, the ability to be expressed in vivo as a single molecule biological label attached to any protein of interest without first purifying, labeling, and re-injecting the protein.

In summary, while current labeling methods and materials have enabled myriad bulk studies and many in vitro single molecule experiments, single molecule experiments remain limited by the disadvantages of even the best fluorescent probes. There is a need in the art for new single molecule probes, created with greatly improved photostability, much stronger absorption and emission under weak illumination, facile synthesis and conjugation to proteins, and tunable emission color. Ideally, such fluorescent labels should also be genetically programmable such that proteins under study can be directly labeled intracellularly, without first being overexpressed, purified, labeled, and then reintroduced into cells.

SUMMARY OF THE INVENTION

It is an object of the present invention to overcome, or at least alleviate, one or more of the difficulties or deficiencies associated with the prior art. The present invention fulfills in part the need to identify new, unique strongly fluorescent labels that allow for the facile study of molecules at either single molecule or bulk concentrations. The compositions comprise a water-soluble fluorescent label comprising an encapsulated noble metal nanocluster. In one embodiment, the noble metal nanocluster comprises between 2 and 8 noble metal atoms. In preferred embodiments, the noble metal is selected from the group consisting of gold, silver, and copper. In certain embodiments, the noble metal nanocluster has a varying charge.

Preferably, the fluorescent label exhibits a polarized spectral emission and exhibits a dipole emission pattern. The fluorescent label has a spectral emission that provides information about a biological state, wherein the biological state is selected from the group consisting of a quantitative and qualitative presence of a biological moiety; structure, composition, and conformation of a biological moiety; localization of a biological moiety in an environment; an interaction between biological moieties, an alteration in structure of a biological compound, and an alteration in a cellular process.

Preferably the fluorescent label of the present invention is capable of fluorescing over a pH range of approximately 3 to approximately 8, and the noble metal nanocluster emits greater than approximately $10^6$ photons, greater than $10^7$, greater than $10^8$, or greater than $10^9$ photons before photobleaching. In one embodiment, the encapsulated noble metal nanocluster has a fluorescence quantum yield of greater than approximately 1% and a saturation intensity ranging from approximately 1 to 1000 W/cm$^2$ at a nanocluster spectral excitation maximum.

In certain preferred embodiments, the noble metal nanocluster is encapsulated in a dendrimer. In one embodiment, the dendrimer comprises poly(amidoamine), wherein the poly(amidoamine) dendrimer is selected from the group consisting of a $0^{th}$ generation, $1^{st}$ generation, $2^{nd}$ generation, $3^{rd}$ generation, a $4^{th}$ generation, and a higher generation poly (amidoamine) dendrimer. In another embodiment, the poly (amidoamine) dendrimer is a $2^{nd}$ generation, or a $4^{th}$ generation OH-terminated poly(amidoamine) dendrimer.

In certain other preferred embodiments, the noble metal nanocluster is encapsulated in a peptide. Preferably the peptide is from approximately 5-500 amino acids in length. In other embodiments, the peptide is from approximately 5-20 amino acids in length. In a further embodiment, the peptide comprises a polypeptide sequence as defined in SEQ ID NO:1.

The present invention provides a method of preparing a dendrimer encapsulated noble metal nanocluster capable of fluorescing as described herein, comprising the steps of: a) combining a dendrimer, an aqueous solution comprising a noble metal, and an aqueous solvent to create a combined solution; b) adding a reducing agent; c) adding a sufficient amount of an acidic compound to adjust the combined solution to a neutral range or physiological pH; and d) mixing the pH adjusted, combined solution to allow the formation of a dendrimer encapsulated noble metal nanocluster. The invention further provides a method of preparing a peptide encapsulated noble metal nanocluster capable of fluorescing as described herein, comprising the steps of a) combining a peptide, an aqueous solution comprising a noble metal, and an aqueous solution to create a combined solution; b) adding a reducing agent; c) adding a sufficient amount of an acidic compound to adjust the combined solution to a neutral range pH; and d) mixing the pH adjusted, combined solution to allow the formation of the peptide encapsulated noble metal nanocluster.

The present invention further encompasses methods of using the fluorescent labels described herein in order to study a biological state. The invention provides for a method of monitoring a molecule of interest comprising: a) attaching a water-soluble fluorescent label comprising an encapsulated noble metal nanocluster to a molecule of interest, wherein the fluorescent label emits an emission spectrum over a certain range of visible or near infrared wavelengths; and b) detecting the emission spectrum of the fluorescent label. In certain embodiments, the method further comprises the initial step of attaching a linker molecule to the encapsulated noble metal nanocluster, wherein the linker molecule is capable of attaching the fluorescent label to the molecule of interest. In a preferred embodiment, the molecule of interest is present in a biological sample. In one preferred embodiment, the noble metal nanocluster is encapsulated in a peptide. Preferably, the peptide is expressed in a cell. In one embodiment, the peptide comprises a fusion polypeptide.

DETAILED DESCRIPTION OF THE INVENTION

Figure 1:
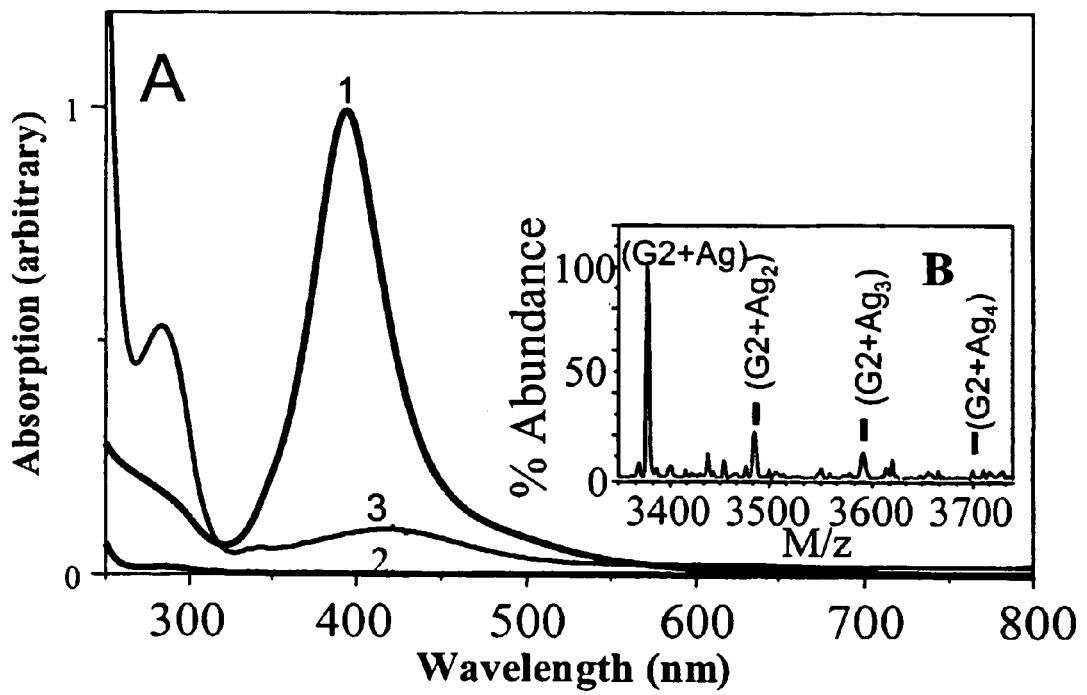
FIG. 1A provides UV-Visible absorption spectra of aqueous silver/dendrimer solutions. (1) indicates strong plasmon absorption (398 nm) characteristic of large, non-fluorescent dendrimer-encapsulated silver nanoparticles prepared through NaBH$_4$ reduction of silver ions in the dendrimer host (1:12 dendrimer:Ag). (2) indicates the absorption spectrum of unreduced, non-fluorescent 1:3 (dendrimer:Ag) solution before photoactivation, and (3) indicates the same solution after photoactivation/photoreduction to produce highly fluorescent silver nanodots.
FIG. 1B provides electrospray ionization mass spectrum of photoactivated G2-OH PAMAM (MW: 3272 amu)-AgNO$_3$ solution. Ag$_n$ nanodot peaks are spaced by the Ag atomic mass (107.8 amu) and only appear in the fluorescent, photoactivated nanodot solutions.

The present invention provides compositions comprising a fluorescent label, methods for preparing the compositions and methods of using the compositions. The compositions of the present invention comprise encapsulated noble metal nanoclusters which are capable of fluorescing. The fluorescent labels provide certain advantages over known fluorescent labels, which include the small size, much stronger absorption and emission under weak illumination, facile synthesis and conjugation to proteins, tunable emission color, and the option to genetically program the labels such that proteins can be directly labeled intracellularly.

The present invention provides for compositions comprising a water-soluble fluorescent label comprising an encapsulated noble metal nanocluster. In one embodiment, the noble metal nanocluster comprises between 2 and 8 noble metal atoms. In preferred embodiments, the noble metal is selected from the group consisting of gold, silver, and copper.

In one embodiment, the fluorescent label exhibits a polarized spectral emission and/or a dipole emission pattern. The fluorescent label has a spectral emission that provides information about a biological state, wherein the biological state is selected from the group consisting of a quantitative and qualitative presence of a biological moiety; location, structure, composition, and conformation of a biological moiety; localization of a biological moiety in an environment; an interaction between biological moieties, an alteration in structure of a biological compound, and an alteration in a cellular process.

Preferably the fluorescent label of the present invention is capable of fluorescing over a pH range of approximately 3 to approximately 8, and the noble metal nanocluster emits greater than approximately $10^6$ photons before photobleaching. In a further embodiment, the noble metal nanocluster emits greater than approximately $10^7$, $10^8$, or greater than $10^9$ photons before photobleaching.

In certain preferred embodiments, the noble metal nanocluster is encapsulated in a dendrimer. In one embodiment, the dendrimer comprises poly(amidoamine), wherein the poly(amidoamine) dendrimer is selected from the group consisting of a $0^{th}$ generation, $1^{st}$ generation, $2^{nd}$ generation, $3^{rd}$ generation, a $4^{th}$ generation, and a higher generation poly (amidoamine) dendrimer. In another embodiment, the poly (amidoamine) dendrimer is a $2^{nd}$ generation, or a $4^{th}$ generation OH-terminated poly(amidoamine) dendrimer.

In certain other preferred embodiments, the noble metal nanocluster is encapsulated in a peptide. Preferably the peptide is from approximately 5-500 amino acids in length. In other embodiments, the peptide is from approximately 5-20 amino acids in length. In a further embodiment, the peptide comprises a polypeptide sequence as defined in SEQ ID NO:1.

The present invention provides a method for preparing a dendrimer encapsulated noble metal nanocluster, comprising the steps of: a) combining a dendrimer, an aqueous solution comprising a noble metal, and an aqueous solvent to create a combined solution; b) adding a reducing agent; c) adding a sufficient amount of an acidic compound to adjust the combined solution to a neutral range or physiological pH; and d) mixing the pH adjusted, combined solution to allow the formation of a dendrimer encapsulated noble metal nanocluster. The invention further provides a method of preparing a peptide encapsulated noble metal nanocluster capable of fluorescing, comprising the steps of a) combining a peptide, an aqueous solution comprising a noble metal, and an aqueous solution to create a combined solution; b) adding a reducing agent; c) adding a sufficient amount of an acidic compound to adjust the combined solution to a neutral range or physiological pH; and d) mixing the pH adjusted, combined solution to allow the formation of the peptide encapsulated noble metal nanocluster.

The present invention further encompasses methods of using the fluorescent labels in order to study a biological state. The invention provides for a method of monitoring a molecule of interest comprising: a) attaching a water-soluble fluorescent label comprising an encapsulated noble metal nanocluster to a molecule of interest, wherein the fluorescent label emits an emission spectrum over a certain range of visible and near infrared wavelengths; and b) detecting the emission spectrum of the fluorescent label. In certain embodiments, the method further comprises the initial step of attaching a linker molecule to the encapsulated noble metal nanocluster, wherein the linker molecule is capable of attaching the fluorescent label to the molecule of interest. In a preferred embodiment, the molecule of interest is present in a biological sample. In one preferred embodiment, the noble metal nanocluster is encapsulated in a peptide. Preferably, the peptide is expressed in a cell. In one embodiment, the peptide comprises a fusion polypeptide.

The highly fluorescent water-soluble noble metal nanoclusters (nanodots) described herein are easily observed as single nanodots with weak mercury lamp excitation due to their incredibly strong absorption and emission (Peyser et al., Science 2001, 291:103; Peyser et al., J. Phys. Chem. B 2002, 106:7725). With absorption strengths comparable to those of much larger quantum dots, these highly fluorescent and incredibly photostable nanodots are useful, in one embodiment, as single molecule and bulk fluorescent biolabels. The creation of stable, biocompatible individual noble metal nanoclusters greatly facilitates the use of these photoactivated nanomaterials as extremely small, bright fluorophores. Such bright, easily synthesized, robust nanomaterials of the present invention will expand the accessibility of single molecule methods by greatly decreasing experimental cost and complexity and providing optically excited fluorophores capable of producing orders of magnitude more photons from individual molecules than currently possible.

One aspect of the invention described herein provides the production and characterization of extremely robust, incredibly bright, photoactivated biological labels that are simultaneously very small, biocompatible, suitable for specific in vitro and in vivo labeling and easily observed on the single molecule level with only weak mercury lamp excitation. At least 20 times brighter than the best organic dyes, the brightness and ease of synthesis enables researchers to easily perform single molecule experiments with standard, inexpensive, lamp-based fluorescence microscopes. As described herein, only a few atoms to few tens of atoms of a noble metal are necessary to generate extremely bright compounds easily observed on the single molecule level. As a result, the proper biocompatible scaffold (generally a dendrimer, genetically optimized peptide, or any other appropriate encapsulating material) encapsulating the noble metal nanoclusters makes these very useful and potentially the smallest possible in vivo and in vitro labels.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compounds, compositions, and methods are disclosed and described, it is to be understood that this invention is not limited to specific noble metals, specific polypeptides, specific dendrimers, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

As used herein, "encapsulating material" refers to a substrate which is capable of attaching to, or physically associating with one or molecules of a noble metal nanocluster. An encapsulating material can provide a means for attaching the noble metal nanocluster indirectly to a molecule of interest, and can protect the noble metal nanocluster from the environment. The attachment or linkage is by means of covalent bonding, hydrogen bonding, adsorption, absorption, metallic bonding, van der Waals forces or ionic bonding, or any combination thereof. As used herein, "encapsulated" means that one or more molecules of the noble metal nanocluster can be physically associated with or entrapped within the encapsulating material, dispersed partially or fully throughout the encapsulating material, or attached or linked to the encapsulating material or any combination thereof, whereby the attachment or linkage is by means of covalent bonding, hydrogen bonding, adsorption, absorption, metallic bonding, van der Waals forces or ionic bonding, or any combination thereof.

The noble metal nanoclusters encompassed by the present invention can be encapsulated by any suitable encapsulating material, which includes, but is not limited to, a dendrimer, a polypeptide, a surfactant, and a non-dendrimer polymer. In one embodiment, the dendrimer is a PAMAM dendrimer. In another embodiment, the polypeptide comprises a sequence ranging form 5-500 amino acids in length. In another embodiment, the polypeptide comprises an antibody.

As used herein with respect to a dendrimer, for example, "encapsulated" means that the one or more molecules of the noble metal nanocluster can be physically associated with or entrapped within the core of the dendrimer, dispersed partially or fully throughout the dendrimer, or attached or linked to the dendrimer or any combination thereof, whereby the attachment or linkage is by means of covalent bonding, hydrogen bonding, adsorption, absorption, metallic bonding, van der Waals forces or ionic bonding, or any combination thereof. Since the size, shape and functional group density of the dendrimers can be rigorously controlled by well-known methods, there are many ways in which the carried material (i.e. the noble metal nanoclusters) can be associated with the dendrimer. For example, (a) there can be covalent, coulombic, hydrophobic, or chelation type association between the carried material(s) and entities, typically functional groups, located at or near the surface of the dendrimer; (b) there can be covalent, coulombic, hydrophobic, or chelation type association between the carried material(s) and moieties located within the interior of the dendrimer; (c) the dendrimer can be prepared to have an interior which is predominantly hollow allowing for entrapment (e.g., physically within or by association with the interior moieties of the dense star dendrimer) of the carried materials within the interior (void volume), (e.g., magnetic or paramagnetic cores or domains created by the chelation and complete or incomplete reduction of metal ions to the zero or non-zero valence state within the dendrimer), these dendrimers containing magnetic interiors can be used for harvesting various bioactive entities that can be complexed with various dendrimer surfaces by use of magnets and the like, wherein the release of the carried material can optionally be controlled by congesting the surface of the dendrimer with diffusion controlling moieties; or (d) various combinations of the aforementioned phenomena can be employed.

As used herein, the term "noble metal" refers to the group of elements selected from the group consisting of gold, silver, and copper and the platinum group metals (PGM) platinum, palladium, osmium, iridium, ruthenium and rhodium. In certain preferred embodiments of the present invention, the noble metal is selected from the group consisting of gold, silver, and copper. In other preferred embodiments, the noble metal is silver. In other preferred embodiments, the noble metal is gold. In other preferred embodiments, the noble metal is copper.

As used herein, the term "nanocluster" refers to an association of 2-27 atoms of a metal. Manufactured nanoclusters are known and are becoming increasingly important in the fields of catalysis, ceramics, semiconductors, and materials science, among others. Their importance is due to the high ratio of surface atoms to interior atoms in nanoclusters. This imparts properties such as high surface reactivities, increased hardness and yield, strength, decreased ductility, liquid-like behavior at low temperature, and size-related chemical, physical, and/or quantum effects that are distinct from those properties of their macro-scale counterparts. At its finest division, an element consists of a single atom. Molecules consist of simple aggregates of a few atoms, and metals and other macrocrystalline solids comprise a crystalline or polycrystalline lattice extending outwards in continuous, three dimensional arrays of atoms. The dimensions of atoms and molecules are measured in angstroms, one angstrom being $10^{-10}$ m or 0.1 nanometers. Crystalline domains in microcrystalline solids such as metals typically are measured on the scale of micrometers. Nanoclusters occupy the transition from the simple atomic state to the nanocrystalline state and may have diameters in the range of about 0.1 to about 3 nm. Preferably, the nanoclusters as described herein comprise approximately 2, 3, 4, 5, 6, 7, 8, 9, 10, 11, 12, 13, 14, 15, 16, 17, 18, 19, 20, 21, 22, 23, 24, 25, 26, or 27 atoms. In other preferred embodiments, the nanoclusters comprise approximately 2-27 atoms, approximately 2-25 atoms, approximately 2-20 atoms, approximately 2-15 atoms, approximately 2-10 atoms, or approximately 2-8 atoms. The size of the nanocluster preferred for encapsulation in an encapsulating material such as a dendrimer or peptide can depend on the type of metal used, the desired emission color, and the particular application.

As used herein, a "nanoparticle" is defined as a particle having a diameter of from approximately 3 to approximately 100 nanometers, having any size, shape or morphology, and comprising a noble metal as defined herein.

As used herein, a "nanodot" is a noble metal nanocluster that is encapsulated in an encapsulating material, such as a dendrimer or a peptide, wherein the encapsulated noble metal nanocluster is capable of fluorescing at a low excitation intensity. Preferably, the encapsulated noble metal nanocluster has a fluorescence quantum yield of greater than approximately 1% and has a saturation intensity ranging from approximately 1 to 1000 W/cm$^2$ at a nanocluster excitation maximum. In certain embodiments, the fluorescence quantum yield is greater than approximately 2%, 3%, 4%, 5%, 10%, 15%, 20%, 25%, 30%, 35%, 40%, 45%, 50%, 60% or higher. In certain embodiments, the saturation intensity ranges from approximately 1-1000 W/cm$^2$, from approximately 10-800 W/cm$^2$, or from approximately 10-500 W/cm$^2$. The excitation maximum varies between nanoclusters, and is dependent at least on the type of metal atom, and the number of metal atoms in the nanocluster. The excitation maximum for a nanocluster is readily determined by one of ordinary skill in the art using means that are well known in the art.

As used herein, the term "saturation intensity" refers to the intensity at which the absorption of the molecule saturates and is no longer linear with respect to excitation intensity. At the saturation intensity for the non-linear absorption of a molecule, multiphoton absorption is no longer dependent on the intensity raised to the power of the nonlinear interaction. The quantum yield is defined as the ratio of the number of photons emitted to the number of photons absorbed.

As used herein, the term "water-soluble" refers to the ability to dissolve and/or form a suspension in an aqueous solution. While the fluorescent label may visibly dissolve in an aqueous solution, it is at least temporarily dispersible or capable of forming a suspension in an aqueous solution.

As used herein, the term "fluorescence" or "fluorescent" is a physical phenomenon based upon the ability of certain molecules to absorb and emit light at different wavelengths. The absorption of light (photons) at a first wavelength is followed by the emission of photons at a second wavelength and different energy. As used herein, a "fluorescent label" is a molecule which absorbs light at a first wavelength and emits the photons at a second wavelength and different energy. As used herein, a "fluorescent label" is used interchangeably with a "luminescent label," and "fluorescent" and "fluorescence" are used interchangeably with the terms "luminescent" and "luminescence," respectively. As such, fluorescence is meant to include phosphorescence and Raman emission, and all emissions indicated by the term "luminescence." As used herein, the term "saturated fluorescence" refers to the ability of a molecule to fluoresce at all incident intensities. Preferably, the fluorescent label comprises an encapsulated noble metal nanocluster. Preferably, the fluorescent labels of the present invention fluoresce at a low excitation intensity, such as that provided by a mercury lamp. Preferably, the low excitation intensity is approximately 30 W/cm$^2$ at approximately 460 nm. In other embodiments, the excitation intensity can range from <1 W/cm$^2$ up to 10 kW/cm$^2$ at a range of excitation wavelengths from approximately 330 nm to approximately 900 nm. The excitation intensity can vary depending at least on the size of the nanocluster, and the metal comprising the nanocluster, and can be readily determined by one of ordinary skill in the art using methods well known in the art. While the fluorescent label as described herein is capable of fluorescing at a low excitation energy such as by a weak mercury lamp, in one embodiment the fluorescent label can fluoresce when activated by a laser.

The spectral emission can be determined for the fluorescent labels of the present invention. Atoms and collections of atoms (or molecules) can make transitions between the electronic energy levels allowed by quantum mechanics by absorbing or emitting the energy difference between the levels. The wavelength of the emitted or absorbed light is such that the photon carries the energy difference between the two orbits. This energy may be calculated by dividing the product of the Planck constant and the speed of light hc by the wavelength of the light. Thus, an atom or collection of atoms can absorb or emit only certain wavelengths (or equivalently, frequencies or energies) as dictated by the detailed atomic structure of the atoms. When the corresponding light is passed through a prism or spectrograph it is separated spatially according to wavelength. The corresponding spectrum may exhibit a continuum, or may have superposed on the continuum bright lines (an emission spectrum). Thus, emission spectra are produced when the atoms do not experience many collisions (because of the low density). The emission lines correspond to photons that are emitted when excited states in the molecule or collection of atoms make transitions back to lower-lying levels. In a preferred embodiment of the present invention, the spectral emission of the fluorescent label is polarized. In other embodiments, depending on nanocluster properties, the emission may exhibit different degrees of polarization. In certain embodiments, the encapsulated noble metal nanocluster exhibits a dipole emission pattern. Preferably, the spectral emission characteristics of the fluorescent label are at least partially determined by one or more characteristics selected from the group consisting of: the encapsulating material used, the generation of the dendrimer, the pH of the test environment, the pH of the environment in which the nanodot is formed, the affinity of the peptide for the noble metal nanocluster which is determined by the peptide sequence, the size of the nanocluster, and the specific noble metal used to form the encapsulated noble metal nanocluster.

Preferably the noble metal nanocluster has a varying charge. As used herein, the term "varying charge" refers to the fact that a noble metal nanocluster can be completely or incompletely reduced, or can be negatively charged. In certain applications, a noble metal nanocluster of a certain charge may be preferred. The charge of a noble metal nanocluster is readily determined by one of ordinary skill in the art using well-known methods.

The noble metal nanoclusters of the present invention are preferably less than 3 nm in diameter, and can be smaller than 2 nm or 1 nm in diameter. After encapsulation, the encapsulated noble metal nanoclusters can range in diameter from less than 1 nm to approximately or greater than 15 nm. The size of the encapsulated noble metal nanocluster is largely dependent on the encapsulating material used. For example, in one embodiment, an antibody such as IgG is used to encapsulate the noble metal nanocluster. These antibodies are approximately 10 nm in diameter. Large 10-50 nm encapsulated noble metal nanoclusters can be filtered by the lymphatic system in vivo for imaging purposes.

As used herein, a "dendritic polymer" is a polymer exhibiting regular dendritic branching, formed by the sequential or generational addition of branched layers to or from a core. The term dendritic polymer encompasses "dendrimers,"

which are characterized by a core, at least one interior branched layer, and a surface branched layer. (See Dvornic & Tomalia in Chem. in Britain, 641-645, August 1994.) A "dendron" is a species of dendrimer having branches emanating from a focal point which is or can be joined to a core, either directly or through a linking moiety to form a dendrimer. Many dendrimers comprise two or more dendrons joined to a common core. However, the term dendrimer is used broadly to encompass a single dendron. In the present invention, a preferred dendrimer is a poly(amidoamine) or PAMAM dendrimer, however, the use of other dendrimers is contemplated. Preferably the dendrimer is selected from the group consisting of a $0^{th}$ generation, a $1^{st}$ generation, a $2^{nd}$ generation, a $3^{rd}$ generation, a $4^{th}$ generation or greater generation dendrimer. The dendrimer can have any termination, including, but not limited to a OH terminating, COOH terminating, and $NH_2$ terminating. The generation of the dendrimer selected varies depending on the desired specific application for the encapsulated noble metal nanocluster.

Dendritic polymers include, but are not limited to, symmetrical and unsymmetrical branching dendrimers, cascade molecules, arborols, and the like, though the most preferred dendritic polymers are dense star polymers. The PAMAM dendrimers disclosed herein are symmetric, in that the branch arms are of equal length. The branching occurs at the hydrogen atoms of a terminal —NH2 group on a preceding generation branch.

Even though not formed by regular sequential addition of branched layers, hyperbranched polymers, e.g., hyperbranched polyols, may be equivalent to a dendritic polymer where the branching pattern exhibits a degree of regularity approaching that of a dendrimer.

Topological polymers, with size and shape controlled domains, are dendrimers that are associated with each other (as an example covalently bridged or through other association as defined hereafter) through their reactive terminal groups, which are referred to as "bridged dendrimers." When more than two dense star dendrimers are associated together, they are referred to as "aggregates" or "dense star aggregates."

Therefore, dendritic polymers include bridged dendrimers and dendrimer aggregates. Dendritic polymers encompass both generationally monodisperse and generationally polydisperse solutions of dendrimers. The dendrimers in a monodisperse solution are substantially all of the same generation, and hence of uniform size and shape. The dendrimers in a polydisperse solution comprise a distribution of different generation dendrimers.

Dendritic polymers also encompass surface modified dendrimers. For example, the surface of a PAMAM dendrimer may be modified by the addition of an amino acid (e.g., lysine or arginine).

As used herein, the term "generation" when referring to a dendrimer means the number of layers of repeating units that are added to the initiator core of the dendrimer. For example, a $1^{st}$ generation dendrimer comprises an initiator core and one layer of the repeating unit, and a $2^{nd}$ generation dendrimer comprises an initiator core and two layers of the repeating unit, etc. Sequential building of generations (i.e., generation number and the size and nature of the repeating units) determines the dimensions of the dendrimers and the nature of their interior.

Methods for linking dendrimers to biological substrates are well known to those of skill in the art, and include the use of linker molecules. For example, thiol-reactive species can be made by coupling the dendrimer hydroxyl group to the isocyanate end of the bi-functional cross-linker, N-(p-maleimidophenyl)isocyanate, leaving a thiol-reactive maleimide for coupling to proteins.

As used herein, the term "photobleaching" comprises all processes, which result in the reduction of the intensity of fluorescent light generated at the wavelength of excitation. In embodiments of the present invention, the noble metal nanocluster emits greater than approximately $10^6$, $10^7$, or $10^8$ photons before photobleaching. In a more preferred embodiment, the noble metal nanocluster emits greater than approximately $10^9$ photons before photobleaching. Photobleaching is readily assessed by one of ordinary skill in the art.

In certain preferred embodiments of the present invention, when the encapsulated noble metal nanoclusters are excited, greater than approximately 80% of the noble metal nanoclusters fluoresce for greater than approximately 30 minutes. Preferably, the noble metal nanoclusters fluoresce at a continuous excitation energy of approximately 300 W/cm$^2$ at 514.5 nm or 476 nm. In another embodiment, preferably greater than approximately 90% of the noble metal nanoclusters fluoresce for greater than approximately 30 minutes. In other embodiments, greater than 80%, or greater than 90% of the nanoclusters have a fluorescence quantum yield of greater than approximately 1% and a saturation intensity that ranges from 1-1000 W/cm$^2$ with emission continuing for greater than 30 minutes.

In one embodiment, a dendrimer encapsulated noble metal nanocluster is used to deliver noble metal nanoclusters across biological membranes to a peptide that strongly binds the noble metal nanocluster. The strength of binding to the noble metal nanocluster is readily determined by one of ordinary skill in the art, and can include a visual estimation of the intensity of the fluorescence. In a preferred embodiment, the dendrimer is a lower generation dendrimer, such as a $0^{th}$ generation, $1^{st}$ generation, or $2^{nd}$ generation. In other embodiments, the dendrimer is a higher generation dendrimer, such as a $3^{rd}$ or $4^{th}$ or higher generation dendrimer. In certain embodiments, the peptide binds the noble metal nanocluster at a range of pH. Preferably, the peptide stably binds the noble metal nanocluster at a pH range of between 10 and 1, more preferably between 9 and 2, more preferably between 8 and 3. In other embodiments the peptide stably binds the noble metal nanocluster at a pH of 9, 8, 7, 6, 5, 4, or 3. This embodiment will allow for the facile labeling of proteins both in vitro and in vivo.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule; thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non-nucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. These terms refer only to the primary structure of the molecule. Thus, these terms include, for example, 3'-deoxy-2', 5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules that are present in the natural source of the nucleic acid (i.e., sequences encoding other polypeptides). Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. A nucleic acid is also considered isolated if it has been altered by human intervention, or placed in a locus or location that is not its natural site, or if it is introduced into a cell by transfection. Moreover, an "isolated" nucleic acid molecule can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

In one preferred embodiment, an isolated nucleic acid encoding a peptide that binds a noble metal nanocluster is introduced into a cell, and the peptide is expressed and binds the noble metal nanocluster. In certain embodiments, isolated nucleic acids encoding a peptide that binds the noble metal nanocluster can also be chimeric or fusion polynucleotides. As used herein, a "chimeric polynucleotide" or "fusion polynucleotide" comprises a nucleic acid encoding a peptide that binds the noble metal nanocluster operably linked to a second nucleic acid sequence. Preferably, the second nucleic acid sequence does not bind or does not strongly bind the noble metal nanocluster, and has both a different polynucleotide sequence and encodes a protein having a different function than a nucleic acid encoding a peptide that binds the noble metal nanocluster. Within the fusion polynucleotide, the term "operably linked" is intended to indicate that the nucleic acid encoding a peptide that binds the noble metal nanocluster and the second nucleic acid sequence, respectively, are fused to each other so that both sequences fulfill the proposed function attributed to the sequence used. The second nucleic acid sequence can be fused to the N-terminus or C-terminus of the nucleic acid encoding a peptide that binds the noble metal nanocluster.

Procedures for introducing a nucleic acid into a cell are well known to those of ordinary skill in the art, and include, without limitation, transfection, transformation or transduction, electroporation, particle bombardment, agroinfection, and the like. In certain embodiments, the nucleic acid is incorporated into a vector or expression cassette that is then introduced into the cell. Other suitable methods for introducing nucleic acids into host cells can be found in Sambrook, et al., *Molecular Cloning: A Laboratory Manual.* 2nd Ed., Cold Spring Harbor Laboratory, Cold Spring Harbor Laboratory Press, Cold Spring Harbor, N.Y., 1989, and other laboratory manuals such as *Methods in Molecular Biology,* 1995, Vol. 44, *Agrobacterium protocols,* Ed: Gartland and Davey, Humana Press, Totowa, N.J.

As used herein, the term polypeptide refers to a chain of at least four amino acids joined by peptide bonds. The chain may be linear, branched, circular or combinations thereof. The terms "peptide," "polypeptide," and "protein" are used interchangeably herein. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The invention also provides chimeric or fusion polypeptides. As used herein, an "chimeric polypeptide" or "fusion polypeptide" comprises an polypeptide which binds a noble metal nanocluster operatively linked to a second polypeptide. Preferably the second polypeptide has an amino acid sequence that is not substantially identical to a noble metal nanocluster optimized binding polypeptide, e.g., a polypeptide which does not stably bind a noble metal nanocluster as described herein. As used herein with respect to the fusion polypeptide, the term "operatively linked" is intended to indicate that the two polypeptides are fused to each other so that both sequences fulfill the proposed function attributed to the sequence used. The second polypeptide can be fused to the N-terminus or C-terminus of the polypeptide which binds a noble metal nanocluster. Such fusion polypeptides can facilitate the single molecule or bulk studies and allow for the direct labeling of peptides in vivo or in vitro.

In certain embodiments of the present invention, the peptide which binds the noble metal nanocluster is from approximately 5-1000 amino acids in length, from 1-800 amino acids in length, or from 5-500 amino acids in length. In certain embodiments, the peptide is from approximately 5-10 amino acids in length. In other embodiments, the peptide is from approximately 10-20 or from 20-40 amino acids in length. In one embodiment, the peptide comprises a polypeptide sequence as defined in SEQ ID NO:1.

The present invention further encompasses methods for the preparation of the encapsulated noble metal nanoclusters having the characteristics as described herein. In one embodiment, the method of preparing a dendrimer encapsulated noble metal nanocluster comprises the steps of: a) combining a dendrimer, an aqueous solution comprising a noble metal, and an aqueous solvent to create a combined solution; b) adding a reducing agent; c) subsequently adding a sufficient amount of an acidic compound to adjust the combined solution to a neutral range pH; and d) mixing the pH adjusted, combined solution to allow the formation of a dendrimer encapsulated noble metal nanocluster. In a second embodiment, the method of preparing a peptide encapsulated noble metal nanocluster capable of fluorescing comprises the steps of: a) combining a peptide, an aqueous solution comprising a noble metal, and distilled water to create a combined solution; b) adding a reducing agent; c) subsequently adding a sufficient amount of an acidic compound to adjust the combined solution to a neutral range pH; and d) mixing the pH adjusted, combined solution to allow the formation of the peptide encapsulated noble metal nanocluster.

In these methods, a reducing agent is added to the combined solution to photoactivate the noble metal nanoclusters. Preferably the reducing agent is selected from the group comprising a chemical reducing agent, light, or a combination thereof. In certain embodiments of these methods, light can be used as a reducing agent to photoactivate the noble metal nanoclusters. In certain other embodiments of these methods, a chemical reducing agent can be used as a reducing agent. In one embodiment, light is used in combination with a reducing agent to photoactivate the noble metal nanoclusters. Preferably the process of preparing the encapsulated noble metal nanoclusters is performed at a temperature of between approximately 65° F. to approximately 100° F. More preferably, the temperature of the combined solution from steps a) through c) is between approximately 68° F. to approximately 80° F., and even more preferably between approximately 68° F. to approximately 74° F.

Preferably, the aqueous solution comprising a noble metal used in the preparation of the compounds is selected from the group consisting of $AgNO_3$, $HAuCl_4 \cdot nH_2O$, and $CuSO_4 \cdot nH_2O$. In one embodiment, the aqueous solution comprising a noble metal is $AgNO_3$. In another embodiment, the aqueous solution comprising a noble metal is $HAuCl_4 \cdot nH_2O$. In a further embodiment, the aqueous solution comprising a noble metal is $CuSO_4 \cdot nH_2O$.

In one embodiment, the aqueous solution comprising a noble metal is $HAuCl_4 \cdot nH_2O$, a reducing agent is added to the combined solution, and the pH adjusted, combined solution is mixed for at least one hour to allow the formation of the dendrimer encapsulated gold nanocluster. In another embodiment, the pH adjusted, combined solution is mixed for about 48 hours to allow the formation of a dendrimer encapsulated gold nanocluster. In another embodiment, encapsulated noble metal nanoclusters are created through photoreduction through irradiation with visible or ultraviolet light to allow the formation of a dendrimer encapsulated gold, silver or copper nanocluster.

In another embodiment, when the encapsulating material is a peptide, preferably the noble metal to peptide molar ratio in step a) is approximately 0.1:1. In another embodiment, the noble metal to peptide molar ratio in step a) is less than approximately 0.1:1, and in other embodiments it is greater than 0.1:1, and can be 1:1 or greater.

In certain embodiments, the encapsulated noble metal nanocluster fluorescent labels is present in a biological sample. In certain preferred embodiments, the peptide which encapsulates the noble metal nanocluster is expressed within a cell, also termed "genetically programmed." As used herein, the term "expressed" encompasses the transcription and/or the translation of the peptide. In other embodiments, the peptide encapsulating the noble metal nanocluster is introduced into a biological sample. As used herein, a "biological sample" refers to a sample of isolated cells, tissue or fluid, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including, but not limited to, conditioned medium resulting from the growth of cells in cell culture medium, putatively virally infected cells, recombinant cells, and cell components). The fluorescent labels can be used in a cell from any type of organism, wherein the organism is a prokaryote or a eukaryote. In preferred embodiments of the present invention, the organism is a eukaryote. Non-limiting examples of the eukaryotic cells of the present invention include cells from animals, plants, fungi, protists, and other microorganisms. In certain embodiments, the cells are part of a multicellular organism, e.g., a plant or animal.

As discussed herein, the selection of the composition of the encapsulated nanocluster, as well as the size of the dendrimer or the sequence of the peptide, affects the characteristic spectral emission wavelength of the semiconductor nanocrystal. Thus, as one of ordinary skill in the art will realize, a particular composition of a nanodot as described herein will be selected based upon the spectral region being monitored. For example, nanodots that emit energy in the visible range, or in the red, blue or near-IR range can be designed. In one embodiment, the encapsulated noble metal nanocluster displays increasingly higher energy emission with decreasing nanocluster size.

The water-soluble encapsulated noble metal nanoclusters of the present invention find use in a variety of assays where other, less reliable, labeling methods have typically been used, including, without limitation, fluorescence microscopy, histology, cytology, pathology, flow cytometry, FISH and other nucleic acid hybridization assays, signal amplification assays, DNA and protein sequencing, immunoassays such as competitive binding assays and ELISAs, immunohistochemical analysis, protein and nucleic acid separation, homogeneous assays, multiplexing, high throughput screening, chromosome karyotyping, and the like. The above-described encapsulated noble metal nanocluster fluorescent labels can be used in any reporter molecule-based assay with an acceptable environment.

In certain preferred embodiments, the encapsulated noble metal nanocluster fluorescent label of the present invention is used in single or bulk molecule studies. The invention encompasses methods of monitoring a molecule of interest comprising: a) attaching a water-soluble fluorescent label comprising an encapsulated noble metal nanocluster to a molecule of interest, wherein the fluorescent label emits an emission spectrum; and b) detecting the emission spectrum of the fluorescent label. As used herein, detecting the emission spectrum encompasses determining the optical emission properties of the fluorescent label. Single molecule studies can allow for the determination of aspects of the local environment, ranging from signal strength, orientation, and lifetime, to the emission spectrum of the molecule and the degree of energy transfer with neighboring molecules. Single molecule studies have been used to manipulate individual molecules and to measure the force generated by molecular motors or covalent bonds. The development of new probe technologies allows for real-time observations of molecular interactions and trafficking within living cells. These tools enable individual members of a population to be examined, identified, and quantitatively compared within cellular sub-populations and substructures. Single molecule studies have the potential to provide spatial and temporal information that is impossible to obtain using other, more static techniques. Single molecule studies allow for measurements to be made on the in vivo dynamic movements of single molecules in intracellular space or to observe the behavior of single molecules over extended periods of time. Using single molecule methods, it should be possible to study time trajectories and reaction pathways of individual members in a cellular assembly without averaging across populations. Cellular processes, such as exocytosis, flux through channels, or the assembly of transcription complexes, could be visualized. Individual differences in structure or function generated by allelic polymorphisms should be detectable at the level of the single molecule. Additionally, monitoring the coordinated expression of a gene or group of genes in specific tissues, or at certain developmental stages, can be performed using these technologies. As such, the use of an encapsulated noble metal nanocluster fluorescent probe allows for the determination of a spectral emission that provides information about a biological state. As used herein, the term "biological state" refers to making a determination of condition such as a quantitative and qualitative presence of a biological moiety; structure, composition, and conformation of a biological moiety; localization of a biological moiety in an environment; an interaction between biological moieties, an alteration in structure of a biological compound, and an alteration in a cellular process.

The methods and compositions of the present invention can further comprise the use of a linker molecule wherein the linker molecule is capable of attaching the fluorescent label comprising an encapsulated noble metal nanocluster to a molecule of interest.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (ed.) 1993 Meth. Enzymol. 218, Part I; Wu (ed.) 1979 Meth Enzymol. 68; Wu et al., (Eds.) 1983 Meth. Enzymol. 100 and 101; Grossman & Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif & Wensink, 1982 Practical Methods in Molecular Biology; Glover (ed.) 1985 DNA Cloning Vol. I and II, IRL Press, Oxford, UK; Hames &Higgins (eds.) 1985 Nucleic Acid Hybridization, IRL Press, Oxford, UK; and Setlow & Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Generation of Dendrite-Encapsulated Silver Nanoclusters

Methods

PAMAM is known to sequester metal ions from solution (Crooks et al., Accounts Chem. Res. 2001, 34:181; Ottaviani et al., Macromolecules 2002, 35:5105; Zheng et al., J. Phys. Chem. B 2002, 106:1252; Varnavski et al., J. Chem. Phys. 2001, 114:1962). PAMAM G4-OH and G2-OH dendrimers ($4^{th}$ and $2^{nd}$-generation OH-terminated poly(amidoamine), respectively, Aldrich) were therefore utilized to concentrate, stabilize, and solubilize Ag nanoclusters in both aerated and deaerated aqueous solutions. By dissolving 0.5 μmol G4-OH and 1.5 μmol $AgNO_3$ into 1 ml distilled water (18 MΩ) and adjusting the solution to neutrality with 160 μmol acetic acid, silver ions readily interact with the dendrimer. Usually used to create small nanoparticles (>3 nm diameter), literature preparations generally add small amounts of reducing agents such as $NaBH_4$ (Crooks et al., Accounts Chem. Res. 2001, 34:181; Ottaviani et al., Macromolecules 2002, 35:5105; Zheng et al., J. Phys. Chem. B 2002, 106:1252; Varnavski et al., J. Chem. Phys. 2001, 114:1962). In order to create dendrimer-encapsulated nanoclusters ("nanodots"), not nanoparticles, reducing agents were not added to the reactions. The fluorescence of these solutions was probed by placing a 10-ml drop of the solution on a clean coverslip in ambient air, nitrogen, and/or evacuated (10-5 torr) environments which was then irradiated with blue light (450-480 nm) from a bandpass-filtered mercury lamp through a standard epifluorescence microscope. Results were unaffected by degree of oxygenation or dendrimer generation.

Results

Initially, no visible absorption or fluorescence was observed from these solutions, but, photoactivation was clearly demonstrated by the solution absorption spectra (FIG. 1A) before and after exposure to white light. Initially only the dendrimer contributed to the spectrum with a single absorption at 284 nm. After photoactivation, the solution exhibited two new peaks at 345 nm and 430 nm due to the absorption of small, photoreduced silver nanodots ($Ag_2$-$Ag_8$) (Rabin et al., G. Chem. Phys. Lett. 1999, 312:394; Bonacic'-Koutecky et al., J. Chem. Phys. 2001, 115:10450). The size and geometry differences of the small silver nanodots simultaneously created during photoactivation yielded multicolored fluorescence throughout the visible region. Silver nanoclusters of this size are the only ones known to have strong visible absorption and emission (Rabin et al., G. Chem. Phys. Lett. 1999, 312:394; Bonacic'-Koutecky et al., J. Chem. Phys. 2001, 115:10450; Linnert et al., J. Am. Chem. Soc. 1990, 112:4657; Mostafavi et al., Chem. Phys. Lett. 1990, 167: 193). The small size was confirmed by mass spectrometry of photoactivated fluorescent nanodot solutions (FIG. 1B). Borohydride-reduced solutions yielded larger silver nanoparticles (3-7 nm) with a characteristic strong surface plasmon absorption at 398 nm, but with essentially no fluorescence (FIG. 1A). Thus, since the fluorescent silver nanodots only appeared without the plasmon absorption, they must be much smaller than 3 nm, and are likely smaller than 2 nm.

Correlating with the changes in absorption, fluorescence grew with increasing irradiation time as silver ions were photoreduced inside the dendrimer host. Within ~6 seconds, the field of view was filled with individual blinking fluorescent species, with little subsequent photoactivation (FIGS. 2A-D). These very bright, stable fluorescent features were all highly polarized and exhibited well-defined dipole emission patterns (FIG. 2E; Bartko & Dickson, J. Phys. Chem. B 1999, 103:11237) and blinking dynamics (Lu et al., Science 1998, 282:1877; Dickson et al., Nature 1997, 388:355; Hu et al., J. Am. Chem. Soc. 1999, 121:6936) characteristic of individual emitters. After completion of photoactivation in this silver-limited environment, the fluorescent silver-dendrimer nanodots remained very stable both in average emission intensity and in spectral characteristics. The dendrimer thereby stabilized the nanoclusters and enhanced their optical properties relative to those on AgO films (Peyser et al., Science 2001, 291:103; Peyser et al., J. Phys. Chem. B 2002, 106:7725). Because the binding energy of small Ag nanoclusters is less than the excitation energy, the cage effect of the dendrimer likely acts similarly to that of rare gas matrices (Rabin et al., Chem. Phys. Lett. 1999, 312:394) to stabilize and enhance nanocluster fluorescence by preventing photodissociation. While water is known to quench Ag nanocluster fluorescence on AgO films (Mihalcea et al., J. Am. Chem. Soc. 2001, 123:7172), dendrimer-encapsulated silver nanodots were highly fluorescent and quite stable in water solution. Thus, the photochemically produced Ag nanoclusters were also protected inside the dendrimer, thereby preventing interaction with quenchers in solution.

Electrospray ionization mass spectrometry (ESI-MS) of the photoactivated nanodot solutions showed strong enrichment of dendrimer+$Ag_n$, with n=2-4 over non-photoactivated, and therefore non-fluorescent nanodot solutions (FIG. 1B). In non-photoactivated nanodot solutions, the dendrimer+$Ag_2$ and larger nanocluster peaks were unobservable, clearly indicating emission from dendrimer-encapsulated Ag nanoclusters ranging in size from 2 to at most 8 atoms once the solutions are photoactivated (Zheng & Dickson, J. Am. Chem. Soc., 2002, 124:13982-13983).

Figure 3:
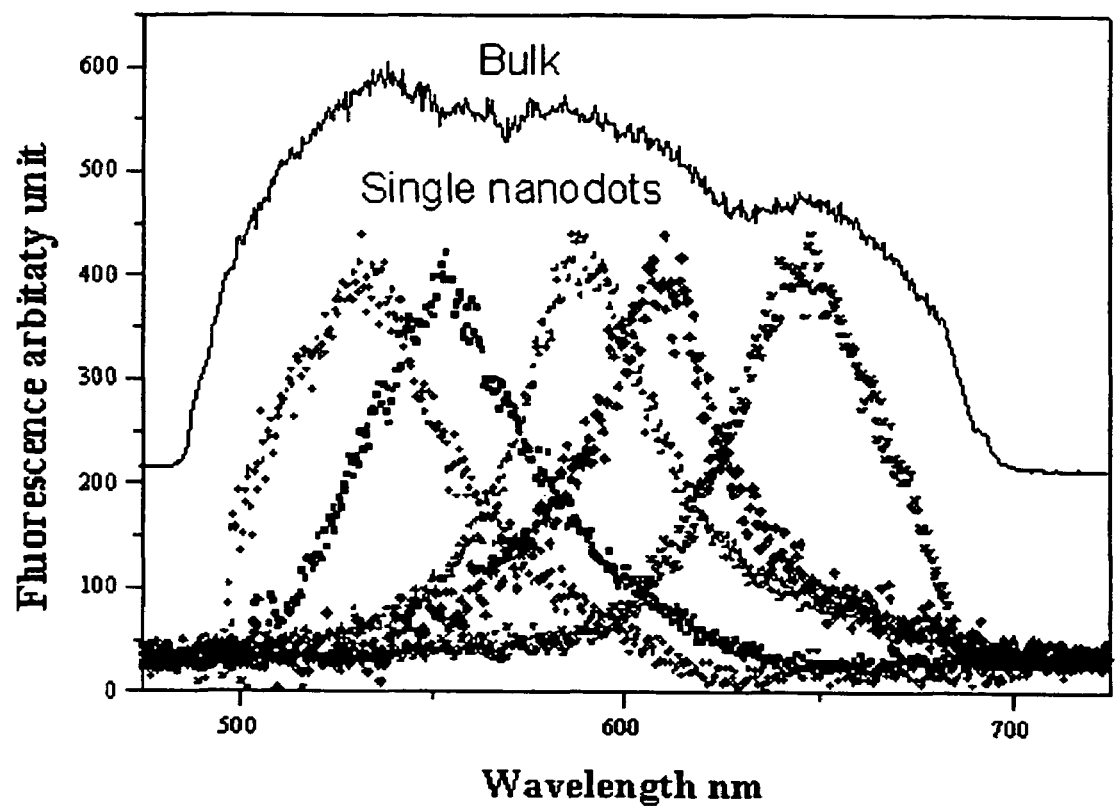
FIG. 3 shows room temperature single nanodot confocal fluorescence spectra (476-nm Ar$^+$ laser excitation, 496-nm long-pass filter, dispersed by a 300-mm monochrometer). Emission maxima for the five typical nanodots shown are 533 nm, 553 nm, 589 nm, 611 nm, and 648 nm. The ensemble fluorescence spectrum of bulk silver nanodot solutions (top) largely consists of these five spectral types, which are indistinguishable from that on AgO surfaces.

Contrary to studying nanoclusters on AgO films (Peyser et al., Science 2001, 291:103; Peyser et al., J. Phys. Chem. B 2002, 106:7725), single nanocluster spectroscopy was readily performed on these soluble dendrimer-encapsulated silver nanodots. While the bulk spectra of $Ag_n$ on AgO and of the aqueous nanodot solutions (FIG. 3) was indistinguishable, individual Ag nanodots had much narrower and more stable emission spectra than either bulk nanodot samples or individual nanoclusters on AgO films (FIG. 3). Because nanocluster size on AgO films was continually modified with excitation, individual nanoclusters were observed to exhibit large spectral shifts (Peyser et al., Science 2001, 291:103; Peyser et al., J. Phys. Chem. B 2002, 106:7725). In contrast, five stable and easily distinguished fluorescence spectra were obtained from these highly dispersed dendrimer-encapsulated silver nanodots (FIG. 3), suggesting that the bulk spectrum was dominated by as few as five nanocluster sizes. Considerably narrower than those of bulk nanodot films or solutions, room temperature single nanodot fluorescence spectra exhibited no obvious spectral diffusion. Because no additional silver could be incorporated into the nanodot and the dendrimer stabilized the nanodot fluorescence, single nanodot emission was quite stable and robust with maxima at 533 nm, 553 nm, 589 nm, 611 nm and 648 nm, although fluorescence intermittency was readily observed. In comparison to II-VI nanoparticles, these nanodots were very photostable with ~80% of individual features remaining fluorescent for >30 minutes of continuous 514.5 nm or 476 nm excitation at 300 W/cm$^2$. The nanodot photoactivation, blinking, dipole emission patterns, spectral stability, mass spectrometry, and fluorescence was observed only for small sized nanodots, further confirming that individual dendrimer-encapsulated $Ag_n$ nanoclusters less than 8 atoms in size gave rise to the observed emission. No fluorescence was observed in similarly prepared solutions without the dendrimer or solutions prepared without the silver. Crucial to solubility and stabilization, the dendrimer enhouses and protects the nanoclusters, yielding strong emission and providing a silver-limited environment that prevents further photoreduction/nanocluster growth.

Through these methods, very photostable, water-soluble silver nanodots have been successfully created in dendrimers through direct photoreduction in ambient conditions. Such silver nanodots are quite stable and highly fluorescent both in aqueous solutions and in films and are readily observed on the single molecule level with weak mercury lamp excitation (30 W/cm$^2$). With synthetic control of dendrimer attachment (for example, thiol-reactive species can be made by coupling the dendrimer hydroxyl group to the isocyanate end of the bi-functional cross-linker, N-(p-maleimidophenyl)isocyanate, leaving a thiol-reactive maleimide for coupling to proteins), such simple nanomaterials are likely to find use as biological labels, thereby making single molecule studies much more widely accessible without expensive laser sources. The intense photoactivated emission and very long life before photobleaching makes these attractive new nanomaterials for studying chemical and biological systems.

Example 2

Characterization of Individual Ag Nanodots

Figure 2:
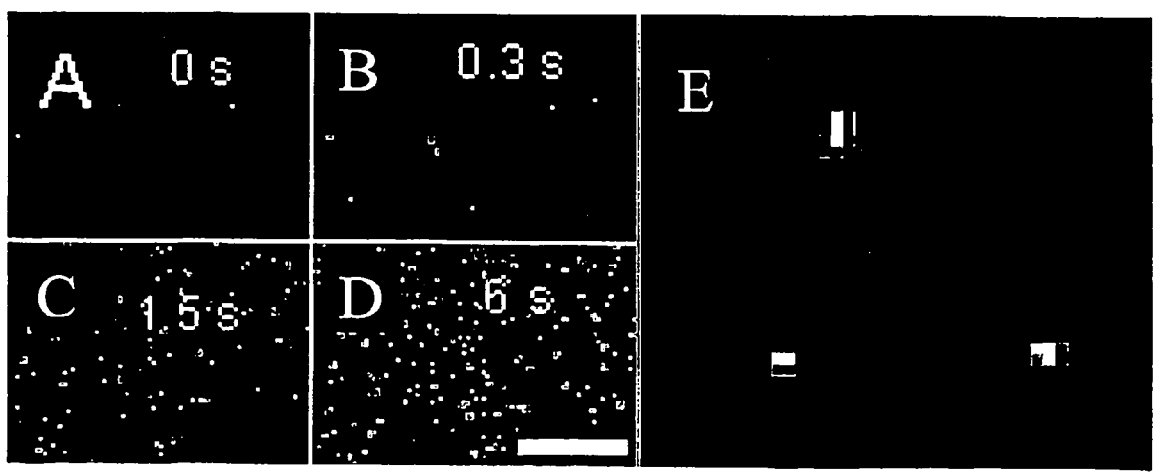
FIGS. 2A-D show mercury lamp excited (450 to 480 nm, 30 W/cm$^2$, scale bar=15 µm) epifluorescence microscopy images demonstrating time-dependent photoactivation of aqueous dendrimer-encapsulated silver nanodots. Each 300 ms CCD frame shows increasing fluorescence with illumination time at 0 seconds, 0.3 seconds, 1.5 seconds, and 6 seconds.
FIG. 2E shows surface-bound silver nanodot emission patterns in aqueous solutions. Indicative of single molecules, the anisotropic emission patterns and fluorescence blinking are easily observable under weak Hg lamp excitation.

A range of PAMAM dendrimer generations (G0-OH through G4-OH with diameters (MW) ranging from 1.5 nm (517 g/mol) to 4.5 nm (14,215 g/mol) were used to yield highly fluorescent $Ag_n$ nanodots. Very bright fluorescence was observed over a pH range of 8.0 to 3.0. These different generations of PAMAM enabled a measure of control over nanocluster distributions: nanodots created with smaller dendrimer generations exhibited different emission spectra than nanodots created with higher dendrimer generations. Not only was nanodot emission extremely stable in spectrum and intensity, but they also exhibited highly polarized emission with very clear and stable dipole emission patterns (FIG. 2E). The observation of emission patterns enabled to employment of the three-dimensional orientational methods developed to follow orientational dynamics either in solution or of immobilized features, as described in Bartko, & Dickson, J. Phys. Chem. B 1999, 103:3053-3056; Bartko & Dickson, J. Phys. Chem. B 1999, 103:11237-11241; and Bartko et al., Chem. Phys. Lett. 2002, 358:459-465.

Figure 4:
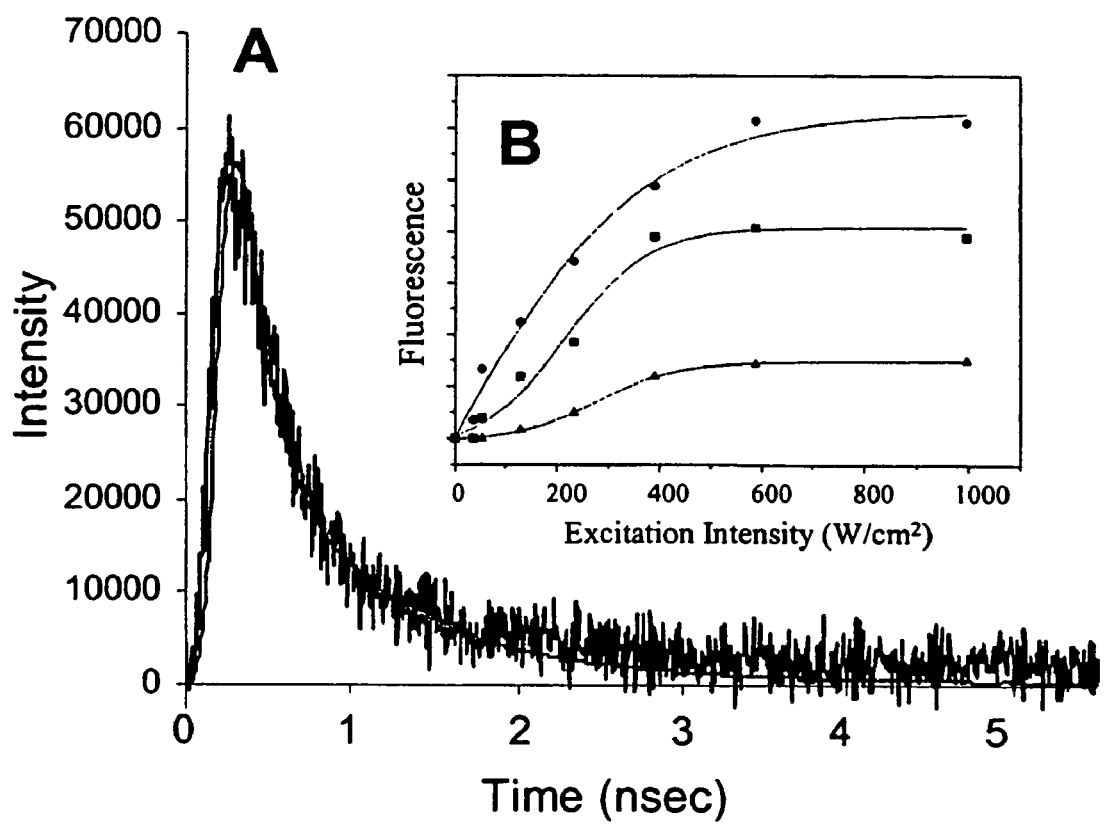
FIG. 4A shows a single nanodot fluorescence lifetime and 5B shows saturation intensity measurements of typical dendrimer-encapsulated nanodots. In 5A, 400-nm excited lifetimes are limited by the 300 ps instrument response, but indicate a sub-100 ps component (92%) and a 1.6 ns component (8%) after deconvolution. In 4B, saturation occurs at ~400 W/cm$^2$ (using off resonant, 514.5-nm excitation), with total intensity differences arising from variations in quantum yields among various nanodots. The organic dye, DiIC$_{18}$, for comparison, has a saturation intensity of 10 kW/cm$^2$. Comparisons to DiI yield a lower estimate of the fluorescence quantum yield of ~30%.

The photophysical parameters of many of these individual Ag nanodots have also been characterized (FIG. 4A). While much smaller than quantum dots, the extremely bright nanodot fluorescence at low excitation intensities (30 W/cm$^2$ at 460 nm, close to the 450-nm excitation maximum) results from the very short fluorescence lifetime. After deconvolution of the instrument response, individual nanodot lifetimes exhibited a primary sub-100 ps component (92%) as measured with time-correlated single photon counting with 400-nm excitation from a doubled Ti:sapphire laser. The nanodots also had a slower (1.6 ns) decay component. The very fast relaxation indicates a very strong connection between ground and excited states, thereby yielding a very strong transition moment from a very small (several atom) nanocluster.

The absorption cross-section of individual nanodots was measured through saturation intensity measurements (FIG. 4B). These were compared with well-characterized single DiIC$_{18}$ molecules that have well-known saturation intensities, lifetimes, and fluorescence quantum yields (Macklin et al., Science 1996, 272:255-258). These experiments indicate that the Ag nanodots have absorption cross sections that are ~20 times stronger than the best organic dyes and nearly identical to the best CdSe quantum dots. Additionally, through comparisons of total numbers of photons absorbed by single DiI molecules and single nanodots, the lower estimates of the nanodot fluorescence quantum yields have been calculated to be at least ~30%. Additionally, these Ag nanodots exhibited at least comparable photostability to much larger II-VI quantum dots, with >90% of individual features remaining fluorescent for >>30 minutes of continuous 514.5-nm excitation at 300 W/cm$^2$. Generally lasting for more than an hour of continuous optical excitation while emitting >10$^6$ photons/sec near saturation, typical individual nanodots emit well over 10$^9$ photons before photobleaching. This is two orders of magnitude more total photons emitted than the best available dyes emit. Consequently these nanodots offer the opportunity to probe both the short time and long time single molecule dynamics within a wide range of biological systems.

Thus, dendrimer-encapsulated water-soluble silver nanoclusters (Ag nanodots) have been created through direct photoreduction in ambient conditions. Such silver nanodots were quite stable in both solution and films and were readily observed on the single molecule level with weak mercury lamp excitation (30 W/cm$^2$) when excited very close to the absorption maximum of 450 nm. With synthetic control of dendrimer attachment, such simple nanomaterials are very useful as biological labels, thereby making single molecule studies much more widely accessible without expensive laser sources. The intense photoactivated emission and very long life before photobleaching makes these attractive new nanomaterials for studying biological systems.

Example 3

Generation of Dendrite-Encapsulated Gold Nanoclusters

Previous studies have yielded fluorescent, surface passivated gold nanoclusters ranging in size from 28 atoms to smaller particles (<1.2 nm) with emission in the near IR (Link et al., J. Phys. Chem. B 2002, 106:3410-3415), red (Huang & Murray, J. Phys. Chem. B 2001, 105:12498-12502), and blue (Wilcoxon et al., J. Chem. Phys. 1998, 108:9137-9143), with increasingly higher energy emission with decreasing nanocluster size. Although Au nanoclusters with million-fold enhanced fluorescence quantum yields $\phi_F$, relative to that of bulk gold films (Mooradian, A. Phys. Rev. Lett. 1969, 22:185-187), have been created, the 10$^{-3}$ to 10$^{-4}$ quantum yields and polydisperse nanoparticle size distributions have precluded them from being good fluorophores (Link et al., J. Phys. Chem. B 2002, 106:3410-3415; Huang & Murray, J. Phys. Chem. B 2001, 105:12498-12502). The present invention discloses water-soluble, monodisperse, blue-emitting Au$_8$ nanodots that when encapsulated in and stabilized by biocompatible PAMAM dendrimers (Tomalia, Sci. Am. 1995, 272:62-66), exhibited a fluorescence quantum yield of 41±5%, a more than 100-fold improvement over other reported gold nanoclusters (Link et al., J. Phys. Chem. B 2002, 106:3410-3415; Huang & Murray, J. Phys. Chem. B 2001, 105:12498-12502). Larger Au$_n$ nanodots have also been produced with strong luminescence throughout the visible region.

Figure 5:
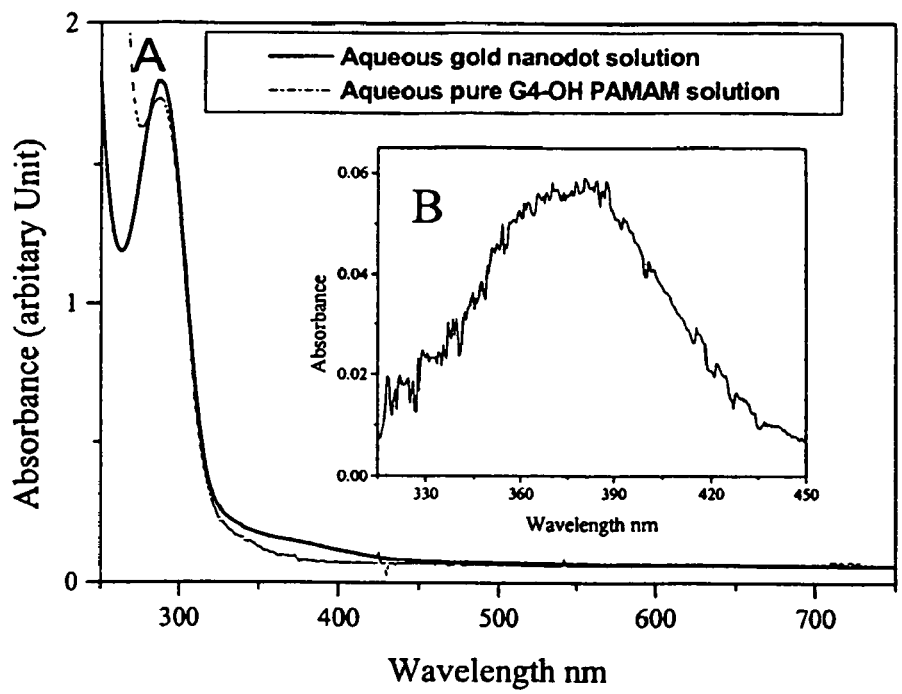
FIG. 5A shows UV-Vis absorption spectra of aqueous gold nanodot and pure dendrimer solutions.
FIG. 5B shows subtraction of absorption spectra in A revealing the 384-nm absorption of PAMAM encapsulated Au nanodots.

Second and fourth generation OH-terminated PAMAM (G2-OH and G4-OH, respectively, Aldrich) were utilized to stabilize and solubilize gold nanoclusters in both aqueous and methanol solutions. By dissolving 0.5 µmol G4-OH or G2-OH and 1.5 µmol HAuCl$_4$.nH$_2$O (Aldrich) into 2 mL of distilled water (18 MΩ), gold ions were sequestered into dendrimers and reduced by slowly adding an equivalent of NaBH$_4$ into the solution. Reduced gold atoms aggregated within the dendrimers to form small nanodots (dendrimer-encapsulated nanoclusters) and large nanoparticles. The solution was stirred for two days until reaction and aggregation processes were completed. Solutions were subsequently purified through centrifugation (13,000 g) to remove the large gold nanoparticles (Crooks et al., Accounts Chem. Res. 2001, 34:181-190; Esumi et al., Langmuir 1998, 14:3157-3159), leaving a clear, colorless, gold nanodot solution. Although weak compared to the 285 nm pure dendrimer peak (see FIG. 5A), a clear absorption spectrum of dendrimer encapsulated gold nanoclusters was obtained by subtracting the pure dendrimer absorption. It can be seen from FIG. 5B that a new absorption band at 384 nm with bandwidth of ~60 nm (FWHM) appeared in the final fluorescent Au nanodot solutions. Contrary to the absorption spectrum of large gold nanoparticles, no surface plasmon absorption at 520 nm was observed from this solution, indicating that the nanodots are smaller than ~2 nm (Crooks et al., Accounts Chem. Res. 2001, 34:181-190; Esumi et al., Langmuir 1998, 14:3157-3159).

Figure 6:
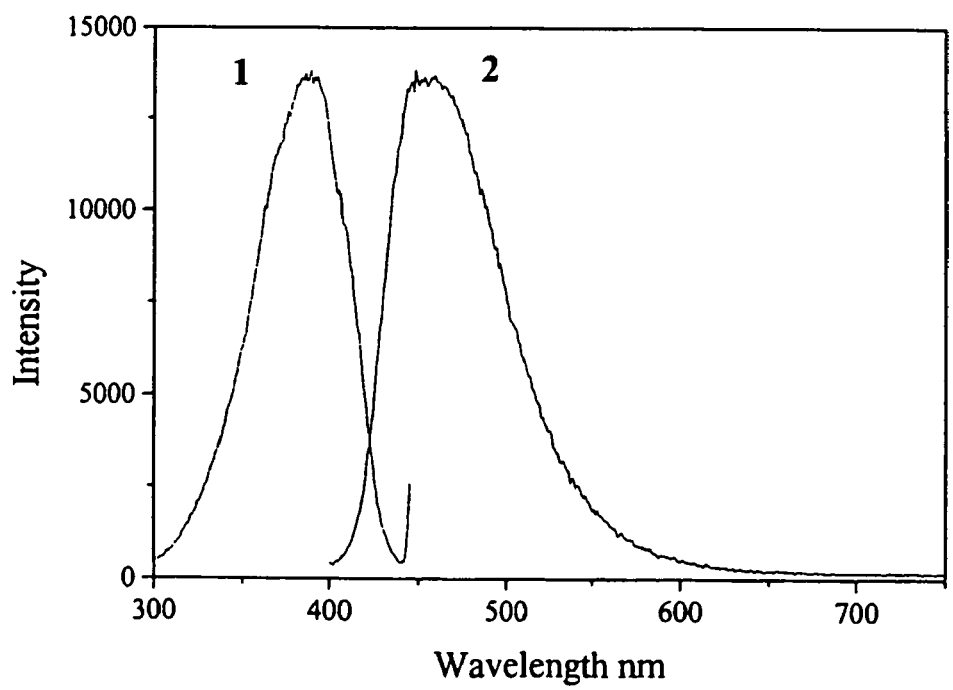
FIG. 6 shows excitation and emission spectra of G4-OH PAMAM encapsulated gold nanoclusters at room temperature. The excitation spectrum is denoted by "1", while the emission spectrum is denoted with "2."

Strong blue luminescence with excitation and emission maxima at 384 nm and 450 nm, respectively, was clearly observed from these dendrimer encapsulated gold nanodot solutions (FIG. 6). The fluorescence excitation maximum and bandwidth were identical to the nanodot absorption band in FIG. 5B. While G2-OH and G4-OH dendrimers yielded indistinguishable fluorescent solutions, under the same synthetic conditions, G0 dendrimers yielded only non-fluorescent solutions with black gold solids. These heterogeneous solutions suggest that, unlike larger $2^{nd}$ and $4^{th}$ generation PAMAM, small $0^{th}$ generation dendrimers do not adequately protect and stabilize gold nanoclusters. Amazingly, for 384-nm excitation, integrated fluorescence quantum yields for G4-OH and G2-OH encapsulated gold nanodots were 41%±5% using similarly emitting quinine sulfate as the reference. The quantum yield further increased in methanol to 52%+5%. The time dependence of the emission showed that there are two lifetime components (FIG. 7A), which are characteristic of gold nanodot emission (Link et al., J. Phys. Chem. B 2002, 106:3410-3415). The short lifetime component was 7.5 ns, which was dominant (93%) in the emission and likely arose from singlet transitions between low lying d orbitals and excited sp bands of gold nanodots. The long lifetime component (2.8 µs, 7%) may be due to a triplet-singlet intraband transition (Link et al., J. Phys. Chem. B 2002, 106:3410-3415; Huang & Murray, J. Phys. Chem. B 2001, 105:12498-12502).

Figure 7:
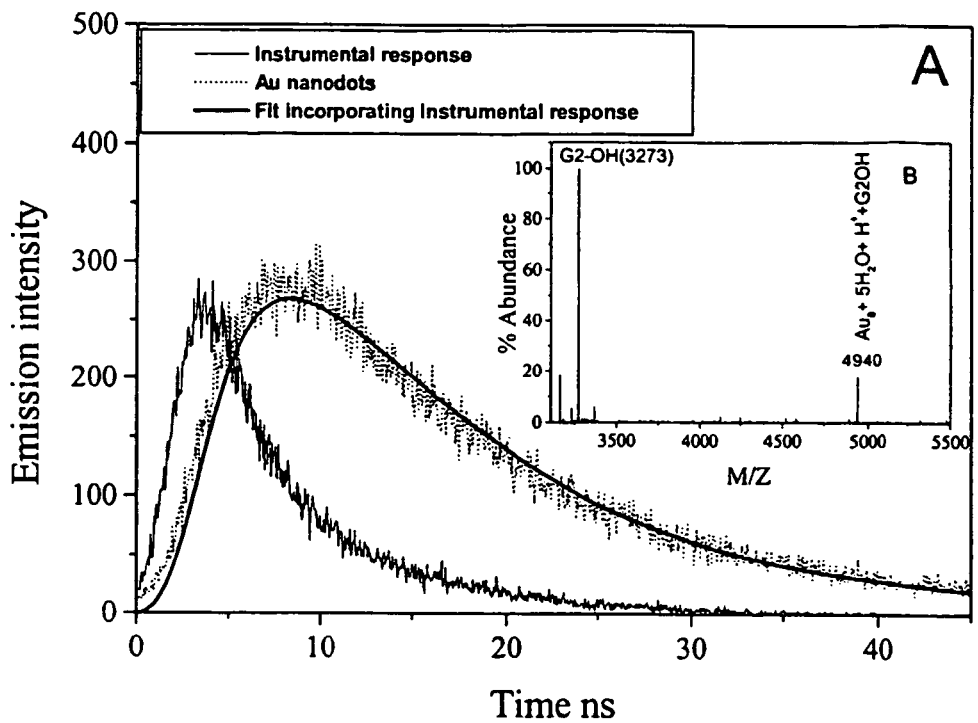
FIG. 7A shows lifetime measurement of gold nanodots in aqueous solution. Instrumental response and nanodot data with fit exhibit the 7.5 ns (93%) and 2.8 µs (7%) lifetimes.
FIG. 7B shows ESI mass spectrum of G2-OH PAMAM encapsulated gold nanodots with expected m/z of 4940 for G2-OH+$Au_8$+$5H_2O$+$H^+$.

The well-defined dendrimer structure enabled analysis of encapsulated nanocluster sizes with electrospray ionization (ESI) mass spectrometry. As shown in FIG. 7B, $Au_8$ was the dominant Au-containing component in the fluorescent solutions and its abundance directly correlates with fluorescence intensity, independent of sample preparation. Depending on the reduction conditions, Au concentrations, and dendrimer generations, different Au-containing peaks can appear in the mass spectra. In all cases (>20 differently prepared samples), blue fluorescence intensity was only related to the abundance of the $Au_8$-containing species observed in the mass spectra. In accord with stable nanoclusters having 8 valence electrons (one from each Au atom; Lin et al., Inorg. Chem. 1991, 30:91-95), this dominant nanocluster was confirmed to be in the overall neutral oxidation state as even 100-fold excess of highly reducing $BH_4^-$ did not alter the nanodot fluorescence. Confirmed through expected shifts relative to the dendrimer parent peak upon dissolution in $D_2O$ instead of $H_2O$, five molecules of water were also found to be associated with the hydrophilic PAMAM dendrimer-Au complex. While five waters appeared to be the favored number, smaller peaks corresponding to $Au_8$ with other numbers of water molecules ranging from one to six were also observed in the mass spectra of other similarly prepared samples. The peaks containing $Au_8$ were only observed in the fluorescent Au nanodot solutions and fluorescence intensities of differently prepared solutions were directly proportional to relative abundance of the $Au_8$ nanodot peaks alone. Additionally, Au nanodot preparations using both $HAuCl_4$ and $AuBr_3$ yielded indistinguishable fluorescent solutions with identical mass spectra. This indicated that the highly efficient blue emission resulted from $Au_8$ nanodots. Different color emission can be produced by adjusting relative Au:dendrimer concentrations to produce larger Au nanodots.

As mentioned above, luminescence from gold nanodots is thought to arise from transitions between the filled d band and sp conduction bands (Link et al., J. Phys. Chem. B 2002, 106:3410-3415; Huang & Murray, J. Phys. Chem. B 2001, 105:12498-12502; Mohamed et al., Chem. Phys. Lett. 2000, 317:517-523). As nanocluster size decreased, the spacings between discrete states in each band increased, leading to a blue shift in fluorescence relative to that from larger nanodots. The more than 100-fold fluorescence quantum yield enhancement over that of differently prepared larger nanoclusters probably results from two factors. The lower density of states present in very small $Au_8$ nanoclusters minimizes internal non-radiative relaxation pathways. Additionally, the larger dendrimer cage better protects these nanoclusters/nanodots from quenchers in solution. This latter interpretation is suggested by the $0^{th}$ generation dendrimer being unable to stabilize fluorescent Au nanodots. Additionally, in the purified solutions there are no large gold nanoparticles to quench the nanodot fluorescence (Dulkeith et al., Phys. Rev. Lett. 2002, 89, art. no.-203002; Huang & Murray, Langmuir 2002, 18:7077-7081).

In conclusion, monodisperse $Au_8$ nanodots were synthesized and stabilized in dendrimer PAMAM aqueous solution. $Au_8$ nanodots show strong size specific emission, and its quantum yield was measured to be ~41% in aqueous solution. Practical applications of gold nanodots as a novel fluorophore become possible due to more than 100-fold enhancement in quantum yield.

Example 4

Generation of Dendrite-Encapsulated Copper Nanoclusters

Second and fourth generation OH-terminated PAMAM (G2-OH and G4-OH, respectively, Aldrich) were utilized to stabilize and solubilize copper nanoclusters in both aqueous and methanol solutions. By dissolving 0.5 µmol G4-OH or G2-OH and 1.5 µmol copper sulfate into 2 mL of distilled water (18 MΩ), copper ions were sequestered into dendrimers and reduced by slowly adding an equivalent of $NaBH_4$ into the solution. Reduced copper atoms aggregated within the dendrimers to form small nanodots (dendrimer-encapsulated nanoclusters) and nanoparticles, leaving a clear, yellow, copper nanodot solution.

Figure 8:
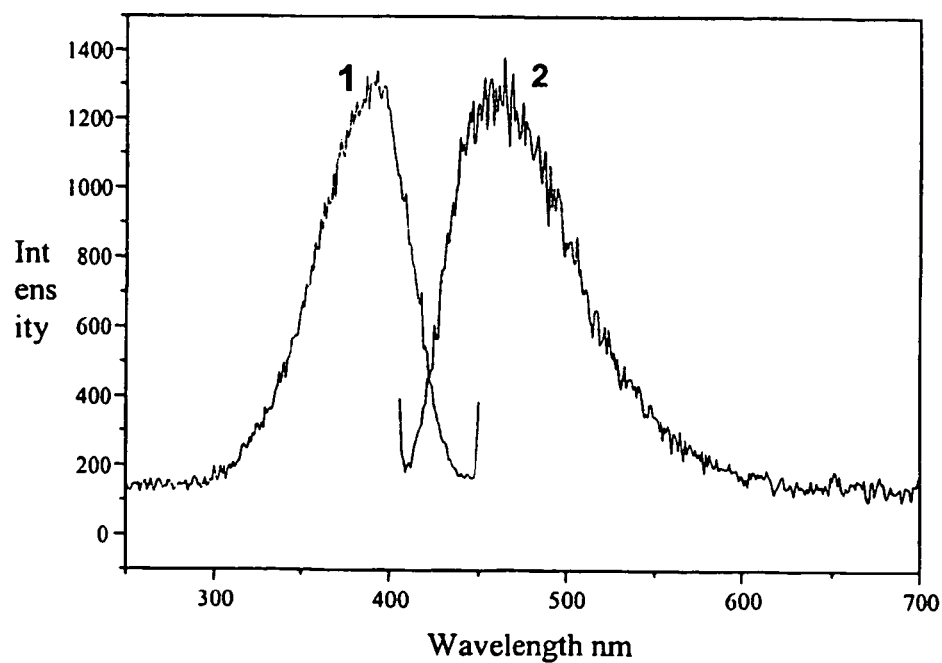
FIG. 8 shows the excitation and emission spectra of PAMAM dendrimer encapsulated copper nanoclusters at room temperature. The excitation spectrum is denoted by "1", while the emission spectrum is denoted with "2."

Strong blue luminescence with excitation and emission maxima at 392 nm and 470 nm, respectively, was clearly observed from these dendrimer encapsulated copper nanodot solutions (FIG. 8). The experiments are repeated with different generations of PAMAM dendrimers, and the emission and excitation spectra determined. The quantum yields are determined for the different generation dendrimer encapsulated copper nanoclusters. The dendrimer structure allows analysis of the encapsulated nanocluster sizes with electrospray ionization (ESI) mass spectrometry. Depending on the reduction conditions, copper concentrations, and dendrimer generations, different copper-containing peaks appear in the mass spectra. Further characterization of the dendrimer encapsulated copper nanoclusters is performed as described in Examples 5-6 for dendrimer encapsulated silver nanodots.

Example 5

Optimizing and Controlling the Generation of Water-Soluble, Photoactivated, Fluorescent Ag Nanodots While dendrimers and chemical reducing agents are commonly employed for synthesis of large metal and semiconducting nanoparticles, much smaller Ag nanodots are readily synthesized simply by adding a 0.5 mM aqueous $AgNO_3$ solution to that of the desired PAMAM dendrimer in the proper molar ratios and adjusting to neutral pH. Generally, no chemical reductants are added, but similar results can be achieved by slowly adding small amounts of $NaBH_4$ to circumvent photoactivation. In solutions without any added chemical reductants, no visible absorption and no fluorescence is observed in these mixtures as long as they are kept in the dark. However, after photoactivation of the entire solution with an unfiltered 100 W Hg lamp for 5 minutes, both visible absorption near 450 nm and strong fluorescence appeared. Much faster photoactivation occurred within small volumes when the solutions were irradiated with higher intensity through the microscope.

While this nanodot synthetic process works very well, it produces a wide distribution of nanodots with fluorescence throughout the visible spectrum. In order to narrow the distribution of synthesized nanodots, spectral properties must be correlated with creation conditions. Certain nanocluster sizes are likely to be created preferentially under specific excitation and concentration conditions. For example, it was noted that total fluorescence intensity and overall emission color are strong functions of the dendrimer generation used: $0^{th}$ generation dendrimers formed primarily yellow and green highly fluorescent nanodots at low Ag:dendrimer ratios of 0.3:1, while $4^{th}$ generation PAMAM required a much higher Ag:dendrimer ratio of 3:1 and produced nanodots of all colors. The reaction conditions are optimized by adjusting both Ag:dendrimer ratios and total concentrations in the reactions with $0^{th}$ through $4^{th}$ or higher generation dendrimers. Working at ratios that only begin to produce fluorescence in each dendrimer generation, the concentration of the smallest emitting nanoclusters will preferentially be enhanced. Aliquots from each solution are irradiated with different wavelength ranges for differing amounts of time. These solutions are compared with those obtained through sub-stoichiometrically added $NaBH_4$ solutions to compare chemical and photoreduction processes. An aliquot of each sample solution is assayed by mass spectrometry using electrospray ionization and compared with the signal from a non-photoactivated solution. Parallel analyses with fluorescence microscopy and ESI-MS identify the spectral signatures of the smallest nanoclusters.

This set of experiments will help elucidate the distribution of Ag nanocluster sizes within the nanodot samples. Because the nanodots contain only a few atoms, nanodot sizes will likely at least loosely follow Poisson statistics (statistics of small numbers) giving predictable populations of silver atoms per dendrimer. Poisson statistics, however, assume that no other interactions are present to further bias the counting statistics. Because different nanoclusters will be more or less stable under different conditions, tuning nanodot creation conditions will yield a modified Poisson distribution, making experimental verification of relative populations critical to identifying the properties of each size nanodot. Adjusting the concentrations should alter the relative populations tempered by the extent of reaction at a given concentration. The offset from Poisson statistics will be a direct measure of the relative equilibrium concentrations and any preferential stabilization of specific nanocluster sizes. Thus, changing concentrations of Ag for a given amount of dendrimer and assaying the mixtures both before and after photoactivation by mass spectrometry and fluorescence microscopy will yield detailed information on the equilibrium constants governing nanodot formation. These experiments will determine the necessary Ag concentrations to preferentially produce the desired silver nanocluster size within the nanodots and the equilibrium constants for each PAMAM generation.

Additionally, the numbers of nanodots of a given color will be counted in the fluorescence microscope field of view using a color CCD camera and fluorescence spectrometer. Image simulation, fitting, and processing software has been written in IDL (Interactive Data Language, Research Systems, Inc.), an open shell programming environment that is ideal for image and mathematical processing. While measuring single molecule fluorescence spectra can be a tedious method of doing this, a representative sample of individual nanodots is probed with the spectrometer to determine the number of differently emitting particles present in a given sample. Once spectral purity and narrowness of individual nanodot emission is confirmed, individual features is counted with a color CCD camera. A single-chip CCD with a standard mosaic filter to produce color images uses 4 pixels (one detecting red, one for blue, and two for green) to generate one composite color pixel. Small, diffraction limited features do not cover enough pixels to yield an accurate color on single chip color CCDs. When detected by such a camera, any small change in sample position will actually be registered as a color change in the emission due to detection by different numbers of red, blue and green pixels. Because of the small size of each feature, a 3-chip CCD will give accurate color information. Using a three-chip CCD, the emission color of each particle will be identified and user-written particle counting software will be employed to automatically count the numbers of each color nanodot. The distribution of fluorescent colors from individual nanodots will be directly correlated with the mass spectrum of each photoactivated or chemically reduced solution to assign the colors to specific nanocluster sizes within each type of nanodot solution. The spectrometer will characterize the spectral width of nanodot emission while the CCD only gives overall color, but with higher sensitivity and time resolution. Thus, the combination is important for accurately characterizing the individual nanodots and their distribution resulting from a given set of creation conditions.

Example 6

Optimizing the Synthesis of Specific Ag Nanodot Sizes

The known pH sensitivity of PAMAM dendrimers and Ag ions and atoms is used to control Ag nanocluster size and therefore control spectral properties. PAMAM is well-known to increase in size with decreasing pH (Kleinman et al., J. Phys. Chem. B 2000, 104:11472-11479; Lee et al., Macromolecules 2002 35:4510-4520; and Bosman et al., Chem. Rev. 1999 99:1665-1688). This size change makes the dendrimer exterior significantly more permeable and creates larger cavities to accommodate nanoclusters or even nanoparticles in their interiors. At high pH, the dendrimer is quite compact, thereby preventing ions from reaching the dendrimer core. This size behavior nicely complements the preference of silver for more basic environments. As a result, Ag ions and metal nanoclusters interact strongly with the basic amines on the dendrimer interior. As the pH decreases, the partitioning of Ag to the dendrimer interior should increase significantly. The increased dendrimer permeability and preference of Ag to interact with the dendrimer interior at acidic pH both suggest that larger nanoclusters should be more readily formed at low pH. Since pH has a more significant effect on higher dendrimer generations, the pH studies will be performed with $4^{th}$ generation G4-OH and G4-$NH_2$ PAMAM dendrimers. This scheme is used to preferentially shift nanodot size distributions to larger and smaller sizes. As a function of pH, bulk absorption and emission spectra are measured, and individual nanodots of a given color as described above are counted. Nanodot distribution is assayed as a function of both dendrimer generation and pH in order to gain control over nanodot spectral properties. Once the nanodots are created, pH will be returned to pH7 to assay stability of formed nanodots within the PAMAM host. ESI-MS is performed on all such solutions to directly correlate changes in optical properties with changes in Ag nanocluster sizes within the nanodot samples. Together, these methods will enable determination of the spectral properties associated with specific Ag nanocluster sizes within the PAMAM dendrimers.

Photophysical Characterization of Dendrimer-Encapsulated Nanodots.

Bulk lifetime measurements are performed on the nanodots in the time domain utilizing a frequency doubled titanium sapphire laser for excitation at 400 nm (82 MHz repetition rate, 200 fs pulse width), a 10 GHz Si photodiode, and a 20 GSample/sec digital oscilloscope. In repetitive mode, this combination can sample points with 50 ps time resolution. This fast detection system is sensitive enough to work for bulk samples through the optical microscope, but, for individual nanodots, a time correlated single photon counting board (Picoquant) and relatively slow, but very sensitive avalanche photodiodes are used, which together are limited by APD jitter to lifetimes of ~300 ps. With deconvolution of instrument response, the primary fluorescence lifetime component of the Ag nanodots was determined to be ~100 ps. Thus, the faster detection system is employed for facile measurement of sub-100 ps lifetimes on the relatively bright emission from groups of Ag nanodots. If multiple lifetimes are present, deconvoluting the different time components is quite straightforward with time-domain methods.

Absorption cross section measurements are made through comparison with single $DiIC_{18}$ molecules, a dye with a very well-characterized absorption cross section and one that has been worked with on the single molecule level (Bartko, & Dickson, J. Phys. Chem. B 1999, 103:3053-3056; Bartko & Dickson, J. Phys. Chem. B 1999, 103:11237-11241; and Bartko et al., Chem. Phys. Lett. 2002, 358:459-465). Confirming single molecule behavior through identifying blinking species and those simultaneously exhibiting dipole emission patterns allows for the circumvention of not knowing the exact concentration within a given sample, and simply measuring the strength of absorption relative to a single molecule of known absorption cross section and comparing the saturation intensities. Using the combination of individual nanodot spectra, their distributions within a given nanodot solution, and their corresponding absorption cross sections, the concentrations of each nanodot species is determined within a given sample. This will be useful in determining the optical density of a given color nanodot within a given solution and by using the initial concentrations of dendrimer and silver, the equilibrium constants for nanodot formation are determined.

Using the measured concentrations of each size nanodot and its contribution to the total solution absorption, the optical density of a given nanodot type is determined. Through comparisons with methanolic rhodamine 6G solutions, nanodot solutions of the same optical density are prepared. Fluorescence quantum yields are measured through exciting at a wavelength with nanodot optical density identical to that of one of the standard rhodamine solutions. The ratio of rhodamine fluorescence intensity to that of the desired nanocluster when looking within its characteristic spectral window (after accounting for the much smaller, but measured contributions from the other nanoclusters in solution) will directly yield the quantum yield of each nanodot. This ratiometric method enables accurate quantum yield measurements without having to know the absolute nanodot concentration because the number of photons absorbed is the same for both the rhodamine 6G reference and the nanodot being probed. Together, the mass spectrometry and photophysical characterizations of both bulk and single molecule samples will definitively determine the sizes and photophysical signatures of each color of nanodots. This information will also lead to improved synthetic methodologies for preferentially enriching one nanodot size over others.

Fluorescence Stability

Largely unaffected by environmental interactions, the dendrimer-stabilized emission is further explored to yield quantitatively similar emission for a given nanodot in a wide variety of different environs. Such environmental insensitivity is in stark contrast to that of II-VI (e.g. CdSe) quantum dots in which surface passivation is crucial to overall photophysical properties due to the presence of trap states on the surface (Bruchez et al., Science 1998, 281:2013-2016; Chan & Nie, Science 1998 281:2016-2018; Nirmal et al., Nature 1996 383:802-804; Huynh et al., Adv. Mater. 1999 11:923; Alivisatos, Endeavour 1997, 21:56-60; Klimov et al., Phys. Rev. B 2000, 61:R13349-R13352). The dendrimer-encapsulated nanodots appear to circumvent such difficulties by having the chromophore ensconced within the water-soluble dendrimer core. The blinking (fluorescence intermittency) is probed as a function of ionic strength and pH. Commonly used buffers such as phosphate buffers and sodium acetate/acetic acid are used to simultaneously control pH while adjusting ionic strength. Quenchers ranging from acrylamide to dyes with different absorptions are added to each nanodot solution to assay for energy transfer from the Ag nanodot. Stern-Volmer quenching studies are performed to determine the extent of quenching and, therefore, the influence of the dendrimer on the nanocluster stabilization and isolation from the environment. The fast lifetimes, however, suggest that these nanodots will be largely insensitive to quenching. In addition to blinking and total emission intensity, the fluorescence lifetime and spectra will also be measured to assay whether any changes occur due to environmental interactions. With their very strong transitions and short lifetimes, however, they are likely to make excellent acceptors in FRET donor-acceptor pairs. Both bulk and single molecule experiments decipher if any change in photophysical dynamics results from altered blinking dynamics or an average overall reduction in fluorescence efficiency. The host density and size of the dendrimers is also adjusted. Ag nanodot blinking dynamics and photophysical parameters in $0^{th}$ through $4^{th}$ generation PAMAM dendrimers are probed to directly determine the protection afforded by successively larger and higher density dendrimer hosts. These studies will directly assay the extent of penetration of solvent and quenchers into the dendrimer core.

Orientational Dynamics

The orientational dynamics of linearly polarized individual surface bound nanodots are investigated for two reasons: geometry changes of small Ag nanoclusters are thought to result in very different absorption and emission wavelengths (Harbich et al., J. Chem. Phys. 1990, 93:8535-8543; Fedrigo et al., J. Chem. Phys. 1993, 99:5712-5717; Rabin et al., Chem. Phys. Lett. 2000, 320:59-64) and the orientational information may be very useful in biological labeling experiments, whether used for energy transfer measurements or following the orientational motion of individual proteins. This is in contrast to the much larger CdSe quantum dots, which are not linearly polarized, but instead emit in all directions, being characterized by a unique "dark" axis (Empedocles et al., Nature 1999, 399:126-130). Thus, correlating orientational dynamics of the nanocluster with any observed spectral changes will be very important to understanding if geometry changes also give rise to differently colored Ag nanodots. These experiments will also be performed with the 3-chip color CCD to obtain color emission patterns. In order to confirm that the spectrum is indeed narrow single nanodot fluorescence spectra will be taken through the microscope coupled spectrograph using a 150 l/mm diffraction grating. The orientational trajectories are fit to the models of dipolar emission at an interface (Bartko et al., J. Phys. Chem. B 1999, 103:3053-3056; Bartko & Dickson, J. Phys. Chem. B 1999, 103:11237-11241; Hollars & Dunn, J. Chem. Phys. 2000, 112:7822-7830; Hellen & Axelrod, J. Opt. Soc. Am. B-Opt. Phys. 1987, 4:337-350) as viewed through an optical microscope to follow true 3-D nanocluster orientational dynamics resulting from any nanocluster mobility within the dendrimer hosts.

Example 7

Peptide Encapsulation of Silver Nanodots

Attempting to utilize the vast diversity inherent in biological systems (Whaley et al., Nature 2000, 405:665-668; Lee et al., Science 2002, 296, 892-5; and Seeman & Belcher, 2002 Proc. Nat. Acad. Sci., USA, 99 Suppl 2:6451-5), it was demonstrated that a short 9-amino acid peptide can stabilize $Ag_n$ nanocluster fluorescence. A short peptide having the sequence AHHAHHAAD (SEQ ID NO:1) was recently reported to interact with large metal and semiconductor nanoparticles upon $NaBH_4$ reduction (Djalali et al., J. Am. Chem. Soc. 2002 124:13660-13661; Slocik et al., Nano Lett. 2002 2:169-173). Using the gentle photoactivation procedures described herein, very highly fluorescent peptide-encapsulated nanodots at Ag:peptide molar ratios of 0.1:1 were produced without chemical reducing agents. These ratios yielded many more fluorescent species than do the higher ratios necessary for nanodot production within other scaffolds. At equivalent scaffold concentrations, 3:1 Ag:dendrimer ratios are necessary for dendrimer encapsulation, and much larger ratios (with higher Ag concentrations) are necessary to produce fluorescence from BSA (bovine serum albumin), both results strongly suggestive that the peptide preferentially binds the nanoclusters. Such preliminary results indicate that non-specific labeling should not be problematic due to the extremely strong peptide-silver interaction, even for this unoptimized peptide. Additionally, using this peptide, fluorescence images are devoid of nearly all red and orange emitters, indicating a narrower fluorescence distribution than those nanodots stabilized by the larger dendrimers. Thus, the stronger and more specific binding of even this first attempt at peptide encapsulation preferentially creates shorter wavelength-emitting (and presumably smaller) Ag nanoclusters within the peptide scaffold with a narrower size distribution. This result strongly bolsters the hypotheses that highly selective nanodot-binding peptides can be identified through the proposed screening methods, and that different peptides are likely to stabilize nanodots of different sizes/colors.

Extremely small, highly fluorescent and incredibly photostable, water-soluble Ag nanodots were produced consisting of only a few atoms encapsulated by both PAMAM dendrimers and short peptides. The extremely advantageous optical properties have yielded incredibly photostable and strongly absorbing and emitting species with size-dependent emission throughout the visible region. One can utilize single molecule microscopies and water-soluble noble metal nanoclusters to create and characterize even more powerful labeling methods and materials. These specific, multicolored labels enable single molecule experiments with high sensitivity, greatly enhanced ease, and experimental simplicity. New fluorescent probe developments of this type are crucial to the general applicability and utility of single molecule methods in unraveling the complexities of biological systems.

Example 8

Identification of Optimal Peptides for Encapsulation of Silver Nanodots

Because Ag is biocompatible and can be non-toxic, it provides unique opportunities for simultaneously developing the smallest and brightest possible in vivo fluorescent biolabels. These same methods can be applied to gold and copper nanodot formation within peptide scaffolds. Dendrimer-encapsulated nanodots can already be employed as small, extremely bright biocompatible labels. Although much smaller than GFP, the 3.272 kD $2^{nd}$ generation PAMAM dendrimer is still larger than most organic dyes. To further explore the potential of using Ag nanodots as biological labels, specific peptide sequences are identified that can specifically bind to differently sized metal nanoclusters and their true prospects for specific multicolor labeling of biomolecules are assessed. By creating and searching peptide libraries for Ag nanodot fluorescence, the most tightly binding sequences are identified. Nanodots formed within these sequences are assayed for stability, photoactivation, and photophysical properties. The relative stability will also be assessed relative to the dendrimer hosts. In this manner, transfer of the nanocluster is investigated between the dendrimer and the peptides.

Experimental Approach

Many protein-ligand interaction studies make use of the phage display technique for identifying peptides that bind to other molecules (Wolcke & Weinhold, Nucleosides Nucleotides Nucleic Acids 2001, 20:1239-41; Krook et al., Biochem Biophys Res Commun 1994, 204:849-54; Nicholls et al., J. Molecular Recognition 1996, 9:652-7 (1996); Stem & Gershoni, Methods Mol. Biol. 1998, 87, 137-54). Although a powerful approach, phage display requires one of the interaction components to be immobilized on solid surfaces. Application of phage-based peptide library screening has also recently been demonstrated in the synthesis and stabilization of unique inorganic materials (Whaley et al., Nature 2000, 405:665-668; Lee et al., Science 2002, 296:892-895; Seeman & Belcher, Proc. Natl. Acad. Sci. USA 2002, 99:6451-6455). Because the target peptides will stabilize strong Ag nanocluster fluorescence in solution, $Ag_n$-binding peptides are identified with an E. coli based system (FliTrx random peptide display library, Invitrogen) coupled with fluorescence-activated cell sorting (FACS). The combination of the two techniques will allow a solution based screening strategy. The FliTrx peptide library displays peptides on the surface of E. coli using the major bacterial flagellar protein (FliC) and thioredoxin (TrxA). The commercially available FliTrx library is composed of a diverse set of random dodecapeptides inserted into the active site loop of thioredoxin, which is itself inserted into the dispensable region of the flagellin. The random dodecapeptides are constrained by a disulfide bond formed within TrxA. Adding tryptophan to the culture can induce the expression of peptide protein fusion, and this will ensure that all peptide fusions are displayed at the same time. When induced, the fusion protein is exported and assembled into flagella on the bacterial cell surface, allowing display of the constrained peptide. As these peptides are produced on the outside of the E. coli cell in high copy numbers, it is these peptides that will be assayed for stabilization of Ag nanodot fluorescence. The population of bacteria is then sorted according to the fluorescence properties with flow cytometry to isolate those bacteria emitting fluorescence.

Optimization of $Ag_n$ Nanodot Production on Displayed FliTrx Peptides

Optimal photoreduction conditions for peptide encapsulated nanodot formation on the bacterial surface are determined through optical microscopy using the previously identified $Ag_n$ (see Example 7). An oligonucleotide encoding the nonopeptide sequence and flanking BglII and EcoRV recognition sequences is synthesized (Operon Co.) and cloned into the multicloning sites of the pFliTrx vector obtained from Invitrogen Co. This construct will insert the peptide into the nonessential region of flagellin as described above. The plasmid is isolated and transformed into the host strain GI826 (Invitrogen) resulting in the display of the peptide on the surface of E. coli. This strain is then used to identify photoactivation and chemical reduction conditions suitable for creating fluorescent peptide-encapsulated Ag nanodots when screening the FliTrx libraries with FACS. Cell viability is assessed when illuminated with blue light and when exposed to $BH_4^-$ reduction as well as the efficiency of generating Ag nanodots. Initially, the total fluorescence from individual bacteria will be measured as a function of photoreduction time for many different $Ag^+$ concentrations through optical microscopy. This procedure is quite straightforward and consists of photochemically reducing Ag ions with electron donors in solution (Tani & Murofushi, J. Imag. Sci. Technol. 1994, 98:1-9; Stellacci et al., Adv. Mater. 2002, 14:194; Eachus et al., Annu. Rev. Phys. Chem. 1999, 50:117-144). This procedure works well due to the advantageous energy levels of Ag relative to those of electronically excited molecules (Tani & Murofushi, J. Imag. Sci. Technol. 1994, 98:1-9; Marchetti et al., J. Phys. Chem. B 1998, 102:5287-5297; Stellacci et al., Adv. Mater. 2002, 14:194; Eachus et al., Annu. Rev. Phys. Chem. 1999, 50:117-144). Photoreduction provides the opportunity to control the nanocluster size and color due to the different reduction potentials for Ag nanoclusters composed of only a few atoms (i.e. $Ag_{2-8}$). Alternatively, chemical reduction can be employed by slowly adding up to an equivalent of $NaBH_4$ or other reducing agents, thereby also yielding fluorescent nanodots. The conditions producing the most highly fluorescent Ag nanodot labeled E. coli cells will be the initial conditions for all library searching studies. Using the strong fluorescence producing conditions identified, the fluorescent bacterial culture will be washed and subsequently suspended in phosphate buffer for FACS analysis. This washed suspension of E. coli will also be re-assayed for total fluorescence on the microscope stage to assess the stability of fluorescence residing on the bacterial surface during the process of sample preparation.

Identification of Specific Ag Nanodot Binding Sequence Through Random Peptide Display Libraries A commercial display library (Invitrogen) will initially be used that contains a diversity of $1.8 \times 10^8$ to identify peptide sequences that interact specifically with Ag nanoclusters. Prepared libraries will be separated into 50 vials and frozen for individual analysis and optimization of Ag nanodot binding conditions as determined by total fluorescence. Each vial will contain most of the peptide library and will be assayed for optimal $Ag_n$ binding conditions through a low magnification objective on the optical microscope stage. First, the library culture will be grown in the presence of tryptophan for 6 hours to induce the expression of fusion flagellins. The culture will be washed with phosphate buffer and then incubated with silver nitrate to form Ag nanodots by photoreduction.

Flow cytometry is capable of correlating cell/particle size with fluorescence. A dot plot of FSC (forward scatter, to define relative size) and SSC (side-scatter, to define relative granularity) will be generated (CellQuest program) to define a gate that specifies the bacterial population for sorting using FACS. The bacteria will be sorted according to the overall fluorescence intensity distribution. Three fluorescence detecting channels are available: FL1, 530 nm with a 30 nm width, FL2, 585 nm with a 42 nm width, and FL3, 650 nm and above, each or combinations of which can be utilized for cell sorting. It is expected the majority of the bacteria with Ag nanocluster non-binding peptides will have minimal fluorescence and only those with significant fluorescence will be recovered. However, the intensity of fluorescence in each channel will be used in conjunction with the forward scatter to identify highly fluorescent cells resulting from $Ag_n$ binding and stabilization. The collected bacteria will be plated out on ampicillin selection agar plates to isolate single colonies. Each single colony will be saved and tested again with flow cytometry and optical microscopy to confirm the associated fluorescence phenotype. Once the intensity of fluorescence is determined, plasmid DNA will be isolated from those bacteria with bright nanodot fluorescence and the peptide sequence determined by direct sequencing analysis. Alignment of sequences from the positive clones may generate a contiguous consensus peptide sequence; alternatively, a structural motif formed by discontinuous conserved residues may be recognized. The defined sequences will be synthesized by solid phase peptide synthesis, and its binding properties to the Ag nanodots characterized using fluorescence microscopy, photophysical characterizations and mass spectrometry, similar to the studies discussed above.

Creating User-Defined Libraries into FliTrx Peptide Display System

An alternative to the use of a commercial library screen, flagellin display libraries can be generated with different peptide lengths using the pFliTrx vector. Degenerate oligonucleotides of 15 bp (5 a.a.), 27 bp (9 a.a.), 45 bp (15 a.a.), and 60 bp (20 a.a.) flanked by BglII and EcoRV restriction recognition sequences will be synthesized (Operon Co.). The mixtures of oligonucleotides will be digested with these two enzymes and cloned into the pFliTrx vector, which has been cut with the same enzymes. The plasmid isolated from the collection of clones will then be transformed into the test strain G1826, and the screening procedures repeated as described above.

This method utilizes the natural diversity of the amino acids to select for specific Ag nanocluster binding to form a biocompatible, highly fluorescent nanodot. In many ways this is similar to the common method of genetically attaching a $(His)_6$-tag on the N- or C-terminus of a protein of interest to be purified through specific interaction with Ni. Analogously, the identified $Ag_n$-binding peptides defined in this study will specifically and selectively bind Ag nanoclusters, thereby enhancing their fluorescence. Additionally, the multiple fluorescence detection channels in FACS will also enable identification of a suite of peptides that preferentially stabilize different size, and therefore color, nanodots.

Characterization of $Ag_n$ Nanocluster-Binding Peptides

Once optimal peptide lengths and sequences are routinely identified and synthesized, environmental stabilities and photophysical properties of the fluorescent nanoclusters are directly assayed as described for the dendrimer-encapsulated nanodots above. While it is likely that specific sequences will preferentially stabilize specific nanocluster sizes with much narrower emission than possible in PAMAM dendrimer hosts, the same particle counting methods to identify the numbers of each type of nanocluster encapsulated within each flavor of peptide will be characterized. In fact, even in the preliminary peptide used that enables and stabilizes Ag nanodot fluorescence, a narrowing of the nanodot size distribution is seen relative to that upon dendrimer encapsulation. Because of the affinity of $Ag_n$ for more basic residues, larger nanoclusters will likely be preferentially stabilized by more basic sequences. This is likely to impart size and therefore nanodot selectivity in peptide-Ag binding interactions. Consequently, this genetic selection of Ag nanodot binding peptides is likely to result in a variety of peptides, each of which stabilize different nanoclusters. This will result in a range of different programmable labels with different optical properties, each of which can be used as an independent single biomolecule label. Mass spectrometry (ESI and MALDI) will be performed on all peptides that are synthesized and subsequently tested for $Ag_n$ nanodot binding in order to determine the nanocluster size distribution within each identified $Ag_n$-binding peptide and its correlation with the number of emitters of a given color. This correlated single nanodot fluorescence microscopy, bulk absorption and emission, and mass spectrometry analysis for differing peptide and silver ion concentrations will directly characterize the binding constants for each peptide identified through FACS library screening.

Example 9

Transfer of Ag Nanoclusters Between Dendrimers and Peptides

Because silver salts generally have very limited solubility in water, AgCl will likely precipitate out of a biologically relevant solution due to its very small solubility product and the large amount of chloride ions present in biological media. This presents a potential problem for delivering $Ag_n$ nanoclusters to the peptides defined in the studies proposed above, and may limit the direct delivery of highly fluorescent Ag nanoclusters. However, Ag nanoclusters were found to be very stable when encapsulated in the dendrimer hosts and retain their very bright fluorescence at physiological NaCl concentrations. Even the small $2^{nd}$ generation PAMAM dendrimer effectively shields the Ag nanoclusters from AgCl precipitation. In addition, dendrimers are well known to readily transport material contained within their interior across biological membranes (Toth et al., STP Pharma Sci. 1999, 9:93-99; Bielinska et al., Biomaterials 2000, 21:877-887; Luo et al., Macromolecules 2002, 35:3456-3462; Yoo et al., Pharm. Res. 1999, 16:1799-1804; Wiwattanapatapee et al, Pharm. Res. 2000, 17:991-998; Esfand, & Tomalia, Drug Discov. Today 2001, 6:427-436), a valuable property in developing in vivo labeling experiments. As a result, the small PAMAM dendrimers are investigated as vehicles to transfer the Ag nanoclusters directly to the identified peptides that strongly bind Ag nanoclusters. Ag nanodot transfer is investigated with the same screening methods as peptide identification and selection. Instead of optimizing silver ion concentrations for effective labeling of peptides within the FliTrx libraries, the dendrimer-encapsulated nanodot concentrations is adjusted while viewing solutions on the microscope stage (with a 10x objective) to monitor nanodot exchange. Once conditions that label the *E. coli* cells are identified, peptide libraries are specifically screened for those cells containing peptides capable of acquiring the nanodots from the dendrimers. Because flow cytometry can select cells based on scatter and fluorescence, the very small dendrimers are undetectable in both channels. Only the cells are sufficiently large to scatter enough light to initiate collection, thereby avoiding false positives due to dendrimer-encapsulated nanodot fluorescence. Additionally, each bacterium within the FliTrx library has thousands of peptide copies, thus providing the potential for much stronger fluorescence signals. Only those cells exhibiting strong fluorescence and scattered light are collected, grown with ampicillin selection, and sequenced. Such dendrimer to peptide library nanodot transfer is likely to be favored for lower generation PAMAM dendrimers under specific environmental conditions, such as specific pH's at which the dendrimer-encapsulated nanodots can more easily escape. The most pH-stable peptide-encapsulated nanodots are therefore likely to be of great utility in future labeling experiments. This additional screening method will further select for peptides that will preferentially extract Ag nanoclusters from the dendrimer, opening possibilities for facile labeling of proteins both in vitro and in vivo.

We claim:

1. A method of monitoring a molecule of interest comprising: a) attaching a water-soluble fluorescent label comprising an encapsulated noble metal nanocluster to a molecule of interest, wherein the noble metal nanocluster is about 0.1 nm to 2 nm in diameter without encapsulation, and wherein the fluorescent label exhibits an emission spectrum; and b) detecting the emission spectrum of the fluorescent label, and c) correlating the detected fluorescent emission spectrum to the presence of the attached molecule of interest, thereby monitoring the molecule of interest.

2. The method of claim 1, wherein the noble metal nanocluster comprises between 2 and 8 noble metal atoms.

3. The method of claim 1, wherein the noble metal is selected from the group consisting of gold, silver, and copper.

4. The method of claim 1, wherein the encapsulated noble metal nanocluster fluoresces at a low excitation intensity and wherein the encapsulated noble metal nanocluster has a saturation intensity ranging from approximately 1 to 1000 W/cm$^2$ at a nanocluster excitation maximum.

5. The method of claim 4, wherein the low excitation intensity at approximately 460 nm.

6. The method of claim 1, wherein the fluorescent label exhibits a polarized spectral emission and exhibits a dipole emission pattern.

7. The method of claim 1, wherein the fluorescent label has a spectral emission that provides information about a biological state.

8. The method of claim 7, wherein the biological state is selected from the group consisting of a quantitative and qualitative presence of a biological moiety; structure, composition, and conformation of a biological moiety; localization of a biological moiety in an environment; an interaction between biological moieties, an alteration in structure of a biological compound, and an alteration in a cellular process.

9. The method of claim 1, wherein when the fluorescent label is excited, it is capable of fluorescing over a pH range of approximately 3 to 9.

10. The method of claim 1, wherein the noble metal nanocluster emits greater than approximately 10$^6$ photons before photobleaching.

11. The method of claim 1, wherein when a composition comprising more than one noble metal nanocluster is excited, greater than approximately 80% of the noble metal nanoclusters fluoresce for greater than approximately 30 minutes.

12. The method of claim 11, wherein the noble metal nanoclusters fluoresce at a continuous excitation intensity of approximately 300 W/cm$^2$ at 514.5 nm or 476 nm, and wherein the fluorescence is a saturated or an unsaturated fluorescence.

13. The method of claim 1, further comprising the initial step of attaching a linker molecule to the encapsulated noble metal nanocluster, wherein the linker molecule is capable of attaching the fluorescent label to the molecule of interest.

14. The method of claim 1, wherein the molecule of interest is present in a biological sample.

15. The method of claim 1, wherein the size of the fluorescent label is from approximately less than 1 nm to 15 nm in diameter.

16. The method of claim 1, wherein the noble metal nanocluster is encapsulated in a dendrimer.

17. The method of claim 16, wherein the dendrimer comprises poly (amidoamine).

18. The method of claim 17, wherein the poly(amidoamine) dendrimer is selected from the group consisting of a 0$^{th}$ generation, 1$^{st}$ generation, 2$^{nd}$ generation, 3$^{rd}$ generation, a 4$^{th}$ generation, and a higher generation poly(amidoamine) dendrimer.

19. The method of claim 17, wherein the poly(amidoamine) dendrimer is a 2$^{nd}$ generation, or a 4$^{th}$ generation OH-terminated poly(amidoamine) dendrimer.

20. The method of claim 1, wherein the noble metal nanocluster is encapsulated in a peptide.

21. The method of claim 20, wherein the peptide is expressed in a cell.

22. The method of claim 20, wherein the peptide comprises a fusion polypeptide.

23. The method of claim 20, wherein the peptide is from approximately 5-500 amino acids in length.

24. The method of claim 20, wherein the peptide is from approximately 5-20 amino acids in length.

25. The method of claim 20, wherein the peptide is from approximately 20-40 amino acids in length.

26. The method of claim 20, wherein the peptide comprises a polypeptide sequence as defined in SEQ ID NO: 1.

27. The method of claim 1, wherein the noble metal nanocluster is less than about 1 nm in diameter prior to encapsulation.

28. The method of claim 1, wherein the noble metal nanocluster comprises between 2 and 27 noble metal atoms.

29. The method of claim 1, wherein the noble metal nanocluster comprises between 2 and 20 noble metal atoms.

30. The method of claim 1, wherein the noble metal nanocluster comprises between 2 and 15 noble metal atoms.

* * * * *

UNITED STATES PATENT AND TRADEMARK OFFICE
CERTIFICATE OF CORRECTION

PATENT NO. : 7,611,907 B2
APPLICATION NO. : 10/519267
DATED : November 3, 2009
INVENTOR(S) : Dickson et al.

It is certified that error appears in the above-identified patent and that said Letters Patent is hereby corrected as shown below:

At column 1, line 3, insert the following:

--STATEMENT OF GOVERNMENT INTEREST

This invention was made with Government support under Grant No. BES-0323453, awarded by National Science Foundation and under Grant No. R 01 GM68732-01, awarded by National Institutes of Health. The Government has certain rights in the invention.--

Signed and Sealed this
Thirteenth Day of March, 2012

David J. Kappos
*Director of the United States Patent and Trademark Office*